US010137172B2

(12) United States Patent
Johansen et al.

(10) Patent No.: US 10,137,172 B2
(45) Date of Patent: Nov. 27, 2018

(54) ADMINISTRATION REGIME
(71) Applicant: Novo Nordisk A/S, Bagsvaerd (DK)
(72) Inventors: Thue Johansen, Koebenhavn OE (DK); Ann Marie Ocampo Francisco, Copenhagen V (DK); Torsten Christensen, Princeton, NJ (US); Jens Harald Kongsoe, Hoersholm (DK); Trine Ahlgreen, Frederiksberg C (DK)
(73) Assignee: Novo Nordisk A/S, Bagsvaerd (DK)
( * ) Notice: Subject to any disclaimer, the term of this patent is extended or adjusted under 35 U.S.C. 154(b) by 0 days.
(21) Appl. No.: 14/888,118
(22) PCT Filed: Apr. 30, 2014
(86) PCT No.: PCT/EP2014/058842
§ 371 (c)(1),
(2) Date: Oct. 30, 2015
(87) PCT Pub. No.: WO2014/177623
PCT Pub. Date: Nov. 6, 2014
(65) Prior Publication Data
US 2016/0058840 A1 Mar. 3, 2016

Related U.S. Application Data

(60) Provisional application No. 61/830,235, filed on Jul. 22, 2013, provisional application No. 61/821,465, filed on May 9, 2013.

(30) Foreign Application Priority Data

Apr. 30, 2013 (EP) ..................................... 13166093
May 27, 2013 (EP) ..................................... 13169312

(51) Int. Cl.
A61K 38/28 (2006.01)
A61K 38/26 (2006.01)
A61K 45/06 (2006.01)
(52) U.S. Cl.
CPC .............. A61K 38/28 (2013.01); A61K 38/26 (2013.01); A61K 45/06 (2013.01)
(58) Field of Classification Search
CPC ......... A61K 38/26; A61K 38/28; A61K 45/06
See application file for complete search history.

(56) References Cited

U.S. PATENT DOCUMENTS

| | | |
|---|---|---|
| 3,528,960 A | 9/1970 | Haas |
| 3,868,358 A | 2/1975 | Jackson |
| 3,907,676 A | 9/1975 | Jorgensen |
| 4,476,118 A | 10/1984 | Brange et al. |
| 4,669,430 A | 6/1987 | Reinold et al. |
| 4,876,322 A | 10/1989 | Budde et al. |
| 4,983,658 A | 1/1991 | Kress et al. |
| 5,177,058 A | 1/1993 | Dorschug |
| 5,382,574 A | 1/1995 | Jorgensen |
| 5,605,884 A | 2/1997 | Lee et al. |
| 5,646,242 A | 7/1997 | Baker et al. |
| 5,750,497 A | 5/1998 | Havelund et al. |
| 5,830,999 A | 11/1998 | Dunn |
| 5,866,538 A | 2/1999 | Norup et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,211,144 B1 | 4/2001 | Havelund |
| 6,221,837 B1 | 4/2001 | Ertl et al. |
| 6,251,856 B1 | 6/2001 | Markussen et al. |
| 6,335,316 B1 | 1/2002 | Hughes et al. |
| 6,451,762 B1 | 9/2002 | Havelund et al. |
| 6,451,970 B1 | 9/2002 | Schaffer et al. |
| 6,504,005 B1 | 1/2003 | Fridkin et al. |
| 6,620,780 B2 | 9/2003 | Markussen et al. |
| 6,652,886 B2 | 11/2003 | Ahn et al. |
| 6,869,930 B1 | 3/2005 | Havelund et al. |
| 7,229,964 B2 | 6/2007 | Markussen et al. |
| 7,402,565 B2 | 7/2008 | Kjeldsen et al. |
| 7,544,656 B2 | 6/2009 | Sabetsky |
| 7,615,532 B2 | 11/2009 | Jonassen et al. |
| 8,003,605 B2 | 8/2011 | Bayer et al. |
| 8,067,362 B2 | 11/2011 | Kodra et al. |
| 8,404,645 B2 * | 3/2013 | Schlein ............... A61K 9/0019 424/400 |
| 8,691,759 B2 | 4/2014 | Madsen et al. |
| 8,722,620 B2 | 5/2014 | Fynbo et al. |
| 8,796,205 B2 | 8/2014 | Jonassen et al. |
| 8,828,923 B2 | 9/2014 | Jonassen et al. |
| 8,933,021 B2 | 1/2015 | Hubalek et al. |
| 8,962,794 B2 | 2/2015 | Madsen et al. |
| 9,034,818 B2 | 5/2015 | Poulsen et al. |
| 9,045,560 B2 | 6/2015 | Madsen et al. |
| 9,131,722 B2 | 9/2015 | Kim et al. |

(Continued)

FOREIGN PATENT DOCUMENTS

| | | |
|---|---|---|
| AU | 2011252127 B2 | 2/2014 |
| CN | 1829738 A | 9/2006 |

(Continued)

OTHER PUBLICATIONS

WebMD "What is a unit of insulin," available at http://answers.webmd.com/answers/1196453/what-is-a-unit-of-insulin.*

(Continued)

Primary Examiner — Marcela M Cordero Garcia
(74) Attorney, Agent, or Firm — Rosemarie R. Wilk-Orescan

(57) ABSTRACT

The invention relates to a novel administration regime useful in the treatment of diseases or conditions where administration of insulin will be of benefit, as well as to kits for use in the same. In particular, the invention relates to a long-acting or ultra-long acting insulin for use in treating a disease or condition where administration of insulin will be of benefit, wherein the administration of said insulin comprises or consists of the following steps: (a) optionally providing a blood sample to be tested from an individual in need of treatment; (b) taking a single fasting blood (or plasma) glucose measurement from said individual in need of treatment; (c) using the single fasting blood (or plasma) glucose measurement to determine the insulin dose to be administered; and (d) administering the long-acting or ultra-long insulin to the individual at the dose determined in step (c).

5 Claims, 3 Drawing Sheets

(56) References Cited

U.S. PATENT DOCUMENTS

Figure 1:
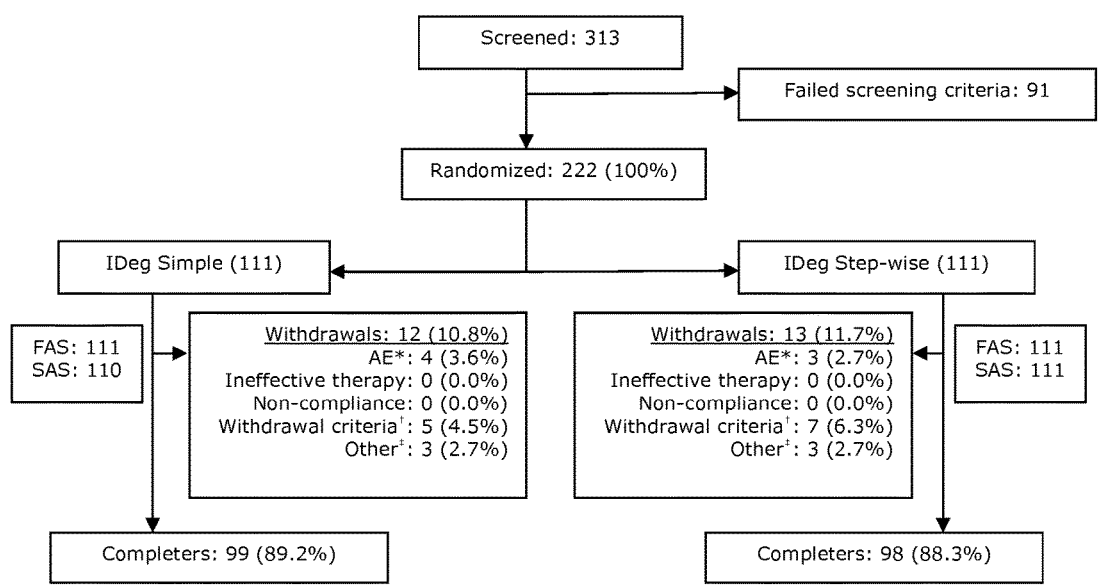

| | | | |
|---|---|---|---|
| 9,447,163 | B2 | 9/2016 | Mollerup et al. |
| 9,481,721 | B2 | 11/2016 | Naver et al. |
| 9,603,904 | B2 * | 3/2017 | Johansen |
| 9,688,737 | B2 | 6/2017 | Madsen et al. |
| 9,839,579 | B2 * | 12/2017 | Weeks .................. C03C 21/002 |
| 9,884,094 | B2 * | 2/2018 | Johansen ............... A61K 38/28 |
| 2002/0045731 | A1 | 4/2002 | Schaffer et al. |
| 2002/0155994 | A1 | 10/2002 | Havelund et al. |
| 2003/0004096 | A1 | 1/2003 | Boderke |
| 2003/0236196 | A1 | 12/2003 | Kerwin et al. |
| 2004/0006000 | A1 | 1/2004 | Langkjaer |
| 2004/0116345 | A1 | 6/2004 | Besman et al. |
| 2004/0138099 | A1 | 7/2004 | Draeger |
| 2005/0054818 | A1 | 3/2005 | Brader et al. |
| 2005/0074866 | A1 | 4/2005 | Grancha et al. |
| 2005/0222006 | A1 | 10/2005 | Havelund et al. |
| 2005/0232899 | A1 | 10/2005 | Balwani et al. |
| 2006/0183668 | A1 | 8/2006 | Jonassen et al. |
| 2008/0076705 | A1 | 3/2008 | Kodra et al. |
| 2009/0074882 | A1 | 3/2009 | Havelund et al. |
| 2009/0137454 | A1 | 5/2009 | Fynbo et al. |
| 2009/0239785 | A1 | 9/2009 | Hubalek et al. |
| 2009/0312236 | A1 | 12/2009 | Beals et al. |
| 2010/0009899 | A1 | 1/2010 | Jonassen et al. |
| 2010/0167990 | A1 | 7/2010 | Poulsen et al. |
| 2011/0152185 | A1 * | 6/2011 | Plum ...................... C07K 14/62<br>514/6.5 |
| 2011/0230402 | A1 * | 9/2011 | Johansen ............... A61K 38/28<br>514/6.3 |
| 2011/0301081 | A1 * | 12/2011 | Becker ................. A61K 9/0019<br>514/6.5 |
| 2013/0261051 | A1 | 10/2013 | Johansen |
| 2014/0073759 | A1 | 3/2014 | Mollerup et al. |
| 2014/0328943 | A1 | 11/2014 | Havelund et al. |
| 2014/0349925 | A1 | 11/2014 | Jonassen et al. |
| 2015/0126439 | A1 | 5/2015 | Johansen et al. |
| 2015/0250857 | A1 | 9/2015 | Andresen et al. |
| 2016/0058840 | A1 | 3/2016 | Johansen et al. |
| 2016/0296602 | A1 | 10/2016 | Johansen |
| 2017/0165327 | A1 | 6/2017 | Andresen et al. |
| 2017/0319664 | A1 | 11/2017 | Johansen |
| 2018/0125946 | A1 | 5/2018 | Johansen |

FOREIGN PATENT DOCUMENTS

| | | |
|---|---|---|
| CN | 101389650 A | 12/2006 |
| CN | 101454019 A | 6/2009 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 925792 A2 | 6/1999 |
| EP | 1153608 A1 | 11/2001 |
| EP | 884053 B1 | 10/2002 |
| EP | 1283051 A1 | 2/2003 |
| EP | 0894095 | 5/2003 |
| EP | 0785713 B1 | 9/2003 |
| EP | 1595544 A1 | 11/2005 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | 38005689 | 5/1963 |
| JP | B S38-5689 | 5/1963 |
| JP | 1254699 | 5/1979 |
| JP | 57-067548 A | 4/1982 |
| JP | 02101022 | 4/1990 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521006 A | 11/2001 |
| JP | 2001-521904 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2004-523589 A | 8/2004 |
| JP | 2006-511441 A | 4/2006 |
| JP | 2006-519253 | 8/2006 |
| JP | 2007-523881 | 8/2007 |
| JP | 2009-522231 | 6/2009 |
| JP | 4808785 B2 | 11/2011 |
| JP | 4959005 B2 | 6/2012 |
| JP | 5026567 B2 | 9/2012 |
| JP | 5331071 B2 | 10/2013 |
| RU | 2160118 C2 | 12/2000 |
| RU | 2164520 C2 | 3/2001 |
| RU | 2352581 C2 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 97/31022 A1 | 8/1997 |
| WO | 98/02460 A1 | 1/1998 |
| WO | 98/05361 A2 | 2/1998 |
| WO | 98/42367 A1 | 10/1998 |
| WO | 98/42368 A1 | 10/1998 |
| WO | 98/47529 A1 | 10/1998 |
| WO | 99/21573 | 5/1999 |
| WO | 99/21578 | 5/1999 |
| WO | 99/21888 A1 | 5/1999 |
| WO | 99/22754 | 5/1999 |
| WO | 99/24071 A1 | 5/1999 |
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 2001/49314 A2 | 7/2001 |
| WO | 02076495 A1 | 10/2002 |
| WO | 2003/002136 A2 | 1/2003 |
| WO | 03/013573 | 2/2003 |
| WO | 03030829 A2 | 4/2003 |
| WO | 03/0053339 A2 | 7/2003 |
| WO | 03/053339 A2 | 7/2003 |
| WO | 03/094951 A1 | 11/2003 |
| WO | 03/094956 A1 | 11/2003 |
| WO | 2004/039392 A2 | 5/2004 |
| WO | 2004/112828 A1 | 12/2004 |
| WO | 2005/005477 A2 | 1/2005 |
| WO | 2005/012347 A2 | 2/2005 |
| WO | 2005/016365 A2 | 2/2005 |
| WO | 2005/021022 A2 | 3/2005 |
| WO | 2005/47508 A1 | 5/2005 |
| WO | 2005/063298 A2 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 06/51103 A2 | 5/2006 |
| WO | 2006/053906 A1 | 5/2006 |

(56) References Cited

FOREIGN PATENT DOCUMENTS

| | | |
|---|---|---|
| WO | 2006/079019 A2 | 7/2006 |
| WO | 2006/082204 | 8/2006 |
| WO | 2006/082205 | 8/2006 |
| WO | 2007/041481 A1 | 4/2007 |
| WO | 2007/074133 A2 | 7/2007 |
| WO | 2007/096431 A1 | 8/2007 |
| WO | 2007/121256 A2 | 10/2007 |
| WO | 2007/128815 A1 | 11/2007 |
| WO | 2007/128817 A2 | 11/2007 |
| WO | 2007/135117 A2 | 11/2007 |
| WO | 2008/034881 A1 | 3/2008 |
| WO | 2008/152106 A1 | 12/2008 |
| WO | 2009/060071 A1 | 5/2009 |
| WO | 2009/063072 A2 | 5/2009 |
| WO | 2010/049488 A1 | 5/2010 |
| WO | 2011141407 A1 | 11/2011 |
| WO | 2012055967 A2 | 5/2012 |
| WO | 2012119007 A1 | 9/2012 |
| WO | 2013037754 A2 | 3/2013 |
| WO | WO2013/164375 * 7/2013 ............. A61K 38/28 |

OTHER PUBLICATIONS

L. Heinemann and J. H. Anderson Jr. Diabetes Technol Ther 6 (5):698-718, 2004.*

Living with Diabetes, available at http://www.diabetes.org/living-with-diabetes/treatment-and-care/medication/?loc=lwd-slabnav, accessed on Jan. 5, 2017).*

Barnett, Clinical Therapeutics (2007) 29(6), 987-999.*

Heller et al. Insulin degludec, an ultra-longacting basal insulin, versus insulin glargine . . . : a phase 3, randomised, open-label, treat-to-target non-inferiority trial. The Lancet, Apr. 21, 2012. vol. 379, 1489-97. (Year: 2012).*

Heise et al. Ultra-long-acting insulin degludec has a flat and stable glucose-lowering effect in type 2 diabetes. Diabetes, Obesity and Metabolism, 2012. vol. 14, pp. 944-950. (Year: 2012).*

Ross SA, et al. Barriers to effective insulin treatment: the persistence of poor glycemic control in type 2 diabetes. Current Medical Research and Opinion 2011, vol. 27(Suppl 3), pp. 13-20.

Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.

Rubin RR et al.. Factors affecting use of insulin pens by patients with type 2 diabetes. Diabetes Care. 2008 vol. 31 pp. 430-432.

Peyrot M and Rubin RR. Factors associated with persistence and resumption of insulin pen use for patients with type 2 diabetes. Diabetes Technology & Therapeutics. 2011 vol. 13 No. 43-48.

Oyer D,et al. Ease of use and preference of a new versus widely available pre-filled insulin pen assessed by people with diabetes, physicians and nurses. Expert Opinion on Drug Delivery. 2011 vol. 8, pp. 1259-1269.

Bailey T,et al Usability and preference evaluation of a prefilled insulin pen with a novel injection mechanism by people with diabetes and healthcare professionals. Current Medical Research and Opinion 2011, vol. 27 pp. 2043-2052.

Nadeau DA,et al. Healthcare professional and patient assessment of a new prefilled insulin pen versus two widely available prefilled insulin pens for ease of use, teaching and learning. Current Medical Research and Opinion 2012;vol. 28.No. 1 pp. 3-13.

Lajara R, et al. Healthcare professional and patient perceptions of a new prefilled insulin pen versus vial and syringe. Expert Opinion on Drug Delivery 2012, vol. 9, pp. 1181-1196.

Bailey T, et al. FlexTouch® for the delivery of insulin: technical attributes and perception among patients and healthcare professionals. Expert Review of Medical Devices 2012, vol. 9, pp. 209-217.

American Diabetes Association,Standards of Medical Care in Diabetes 2012, Diabetes Care 2012,vol. 35(Suppl 1), pp. S11-S63.

American Diabetes Association. Insulin administration. Diabetes Care. 2012 vol. 35, No. 1, pp. S1-S2.

American Diabetes Association. Standards of Medical Care in Diabetes—2014. Diabetes Care. 2014, vol. 37 Suppl 1, pp. S14-S80.

Anderson RM et al. Patient empowerment: results of a randomized controlled trial. Diabetes Care. 1995, vol. 18,No. 7 pp. 943-949.

Barnett et al: Dosing of insulin glargine in the treatment of type 2 diabetes ,Clinical Therapeutics, 2007 vol. 29, No. 6,,pp. 987-999.

Benjamin EM. Self-monitoring of blood glucose: the basics. Clinical Diabetes. 2002, vol. 20, No. 1, pp. 45-47.

Canadian Diabetes Association Clinical Practice Guidelines Expert Committee. Canadian Diabetes Association. Canadian Journal of Diabetes. 2008, vol. 32(Suppl 1)pp. S1-S201.

Davies M, et al.. Improvement of glycemic control in subjects with poorly controlled type 2 diabetes. Diabetes Care. 2005,vol. 28, No. 6, pp. 1282-1288.

Deutsch T et al,Utopia: A Consultation System for Visit-by-Visit Diabetes Management, Medical Informatica. Taylor and Francis.; Basingstoke. GB, 1996, vol. 21, No. 4, pp. 345-358.

Duckworth W. et al.Glucose Control and Vascular Complications in Veterans with Type 2 Diabetes, The new england journal o f medicine, 2009, vol. 360, pp. 129-139.

Gerstein H C et al. A randomized trial of adding insulin glargine vs.avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia treatment) Study, Diabetic Medicines, 2006, vol. 23, No. 7, pp. 736-742.

Holman RR et al.,10-Year Follow-up of Intensive Glucose Control in Type 2 Diabetes,The New England Journal of Medicine, 2008, vol. 359, pp. 1577-1589.

Holman RR et al.A practical guide to Basal and Prandial Insulin therapy, Diabetic Medicine, 1985, vol. 2, pp. 45-53.

International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.

Inzucchi SE et al.Management of Hyperglycemia in Type 2 Diabetes: A Patient-Centered Approach: Position Statement of the American Diabetes Association (ADA) and the European Association for the Study of Diabetes (EASD),Diabetes care, 2012, vol. 35, pp. 1364-1379.

Iwamoto Yasuhi Ko et al: Insulin degludec in Japanese patients with type 1 diabetes mellitus: A randomized controlled trial,Journal of Diabetes Investigation,2013,vol. 4, No. 1, pp. 62-68.

Janka Hans U et al, Combination of oral antidiabetic agents with basal insulin; versus premixed insulin alone in randomized elderly patients with type 2 diabetes mellitus, Journal of the American Geriatrics Society, 2007,vol. 55, No. 2, pp. 182-188.

Kulzer B, et al. Effects of self-management training in type 2 diabetes: a randomized, prospective trial. Diabetic Medicine. 2007, vol. 24, No. 4, pp. 415-423.

LANTUS® (insulin glargine [rDNA origin] injection). sanofi-aventis U.S. LLC, Bridgewater, NJ, USA; 2007. Health Care Professional. Dosing & Titration. Available at: http://www.lantus.com/hcp/titration.aspx. Accessed Nov. 13, 2012.

Liebl A, et al. Direct costs and health-related resource utilisation in the 6 months after insulin initiation in German patients with type 2 diabetes mellitus in 2006: Instigate study. Current Medical Research Opinion 2008,vol. 24, No. 8, pp. 2349-2358.

Meneghini L et al., The usage of a simplified self-titration dosing guideline (303 Algorithm) for insulin detemir in patients with type 2 diabetes-results of the randomized, controlled Predictive TM 303 study. Diabetes Obesity and Metabolism. 2007, vol. 9, pp. 902-913.

Nathan DM et al,Intensive Diabetes Treatment and Cardiovascular Disease in Patients with Type 1 Diabetes,The new england journal of medicine, 2005, vol. 353, No. 25, pp. 2643-2653.

Nathan DM et al.Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.

(56) References Cited

OTHER PUBLICATIONS

Nathan DM et al.The Effect of Intensive Treatment of Diabetes on the Development and Progression of Long-Term Complications in Insulin-Dependent Diabetes Mellitus,The Diabetes Control and Complications Trial Research Group,The New England Journal of medicine, 1993, vol. 329, No. 14, pp. 977-986.
Norris SL, et al. Self-management education for adults with type 2 diabetes: a meta-analysis on the effect of glycemic control. Diabetes Care, 2002, vol. 25, No. 7, pp. 1159-1171.
Ohkubo Y et al. Intensive insulin therapy prevents the progression of diabetic microvascular complications in Japanese patients with non-insulin-dependent diabetes mellitus: a randomized prospective 6-year study,Diabetes Research and Clinical Practice, 1995, vol. 28, No. 2 pp. 103-117.
Peyrot M, et al. Factors associated with injection omission/non-adherence in the Global Attitudes of Patients and Physicians in Insulin Therapy Study. Diabetes Obesity and Metabolism. 2012,vol. 14, pp. 1081-1087.
Peyrot M, et al.. Insulin adherence behaviours and barriers in the multinational Global Attitudes of Patients and Physicians in insulin therapy study. Diabetic Medcine. 2012,vol. 29, No. 5, pp. 682-689.
Philis-Tsimikas A et al.: Insulin degludec once-daily in type 2 diabetes:; Simple or step-wise titration (Begin: Once-Simple Use), Advances in Therapy, 2013,vol. 30, No. 6, pp. 607-622.
Sakharova O V et al.Effects on post-prandial glucose and AGE precursors from two initial insulin strategies in patients with Type 2 diabetes uncontrolled by oral agents, Journal of Diabetes and Its Complications,2012,vol. 26, No. 4, pp. 333-338.
Schnell O, et al. Consensus statement on self-monitoring of blood glucose in diabetes. Diabetes, Stoffwechsel und Herz. 2009, vol. 4, pp. 285-289.
Selvin E et al,.Meta-Analysis: Glycosylated Hemoglobin and Cardiovascular Disease in; Diabetes Mellitus, Annals of internal medicine,2004, vol. 141, pp. 421-431.
The ADVANCE Collaborative Group, Patel A et al.Intensive Blood Glucose Control and Vascular Outcomes in Patients with Type 2 Diabetes, The new England Journal of Medicine, 2008, vol. 358, pp. 2560-2572.
UK Prospective Diabetes Study (UKPDS) Group, Intensive blood-glucose control with sulphonylureas or insulin compared with conventional treatment and risk of complications in patients with type 2 diabetes (UKPDS 33)., Lancet, 1998, vol. 352 (9131), pp. 837-853.
Yeaw J, et al. Cost of self-monitoring of blood glucose in Canada among patients on an insulin regimen for diabetes. Diabetes Therapeutics . Epub ,2012 vol. 3, No. 7, pp. 1-17 doi: 10.1007/s13300-012-0007-6.
Yeaw J, et al. Self-monitoring blood glucose test strip utilization in Canada. Diabetes. 2012;vol. 61(Suppl 1)p. A35.
Yeaw J, et al.. Cost of self-monitoring of blood glucose in the United States among patients on an insulin regimen for diabetes. Journal of Managed Care Pharmacy 2012, vol. 18, No. 1, pp. 21-32.
American Diabetes Association. Insulin administration. Diabetes Care. 2002 vol. 25: pp. S112-S115.
Heise T, et al.. Insulin degludec: four times lower pharmacodynamic variability than insulin glargine under steady-state conditions in type 1 diabetes. Diabetes Obesity and Metabolism , 2012, vol. 14, pp. 859-864.
Heise T, et al. Insulin degludec 200 U/mL is ultra-long-acting and has a flat and stable glucose-lowering effect. Diabetes.2012;, vol. 61(Suppl.1) p. A91.
Korsatko S, et al. Ultra-long-acting insulin degludec: bio-equivalence and similar pharmacodynamics shown for two different formulations (U100 and U200). Diabetologia. 2011 , vol. 54(Suppl. 1) p. S427.
World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.
International Conference on Harmonisation. ICH Harmonised Tripartite Guideline:Guideline for Good Clinical Practice. E6 (R1), Step 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.
Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.
Garg S, et al. Preference for a new prefilled insulin pen compared with the original pen. Current Medical Research & Opinion. 2011 vol. 27 pp. 2323-2333.
Garber AJ, et al; on behalf of the NN1250-3582 BEGINTM BB T2D trial investigators. Insulin degludec, an ultra-long acting basal insulin, versus insulin glargine in Basal-Bolus treatment with meal-time insulin aspart in type 2 diabetes (BEGINTM Basal-Bolus Type 2): a phase 3, randomised, open-label, treat-to-target non-inferiority trial. Lancet.2012, vol. 379, pp. 1498-1507.
Zinman B, et al; on behalf of the NN1250-3579 BEGIN tm Once Long trial investigators. Insulin degludec versus insulin glargine in insulin-naïve patients with type 2 diabetes: a 1-year, randomized, treat-to-target trial (BEGIN tm Once Long). Diabetes Care. 2012 vol. 35 pp. 2464-2471.
Bergenstal R, Bhargava A, Jain RK, et al; on behalf of the NN1250-3672 BEGIN TM Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.
Onishi Y, et al. Superior glycaemic control with once daily insulin degludec/ insulin aspart versus insulin glargine in Japanese adults with type 2 diabetes inadequately controlled on oral drugs: a randomized, controlled phase 3 trial. Diabetes Obesity and Metabolism. 2013 vol. 15, pp. 826-832.
Rakel RE. Improving patient acceptance and adherence in diabetes management: a focus on insulin therapy. Advances in Therapy. 2009, vol. 26 pp. 838-846.
Havelund, S. et al., "The Mechanism of Protraction of Insulin Detemir, a Long-Acting, Acylated Analog of Human Insulin", Pharmaceutical Research, 2004, vol. 21, No. 8, pp. 1498-1504.
Barnett, A.H., "A Review of Basal Insulins," Diabet Med, 2003, vol. 20, No. 11, pp. 873-885.
Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.
Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.
Definition of Moiety From http://dictionary.reference.com/browse/moiety, 2010, pp. 1-3.
Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.
Schlichtkrull, J., "Insulin Crystals", Acta Chemica Scandinavica, 1956, vol. 10, No. 9, pp. 1455-1458.
Vajo et al., "Genetically Engineered Insulin Analogs: Diabetes in the New Millennium," Pharma Rev, 2000, vol. 52, No. 1, pp. 1-9.
Whittingham, J.L. et al., "Crystallographic and Solution Studies of N-Lithocholyl Insulin: A New Generation of prolonged-Acting Human Insulins", Biochemistry, 2004, vol. 42, pp. 5987-5995.
Brange, J et al Diabetic Medicine Neutral Insulin Solutions Physically Stabilized by Addition of ZN2+, 1986, vol. 3, No. 6, pp. 532-536.
Jonassen, I. et al., Pharmaceutical Research 2006, vol. 23, No. 1, pp. 49-55.
Nathan, D. M. et al., "Management of Hyperglycemia in Type 2 Diabetes: A Consensus Algorithm for the Initiation and Adjustment of Therapy," Diabetes Care, 2008, vol. 31, No. 1, pp. 173-175.

(56) References Cited

OTHER PUBLICATIONS

Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.
Hinds et al., "PEGylated insulin in PLGA microparticles. In vivo and in vitro analysis," Journal of Controlled Release, 2005, vol. 104, No. 3, pp. 447-460.
Heller. S R, Current Medical Research and Opinion, "Insulin Analogues", 2002, vol. 18, No. 1, pp. 40-47.
I. Jonassen et al., Diabetologia, "Insulin Degludec: Multi-Hexamer Formation is the Underlying Basis for This New Generation Ultra-Long Acting Basal Insulin", 2010, vol. 53, No. 1, pp. S388.
R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", 2010, vol. 53, No. 1, pp. S389.
Samuel et al. "Studies on the immunogenicity of protamines in humans and experimental animals by means of a micro-complement fixation test." Clin. Exp. Immunol. vol. 33: pp. 252-260. 1978.
Kurtz et al. "Circulating IgG antibody to protamine in patients treated with protamine-insulins." Diabetologica. vol. 25: pp. 322-324. 1983.
Definition of Moiety From http://dictionary.reference.com/browse/moiety, Aug. 26, 2010, pp. 1-3.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, 2010, vol. 53, No. 1, pp. S389.
I. Jonassen et al., "Insulin Degludec: Multi-Hexamer Formation is the Underlying Basis for This New Generation Ultra-Long Acting Basal Insulin", Diabetologia, 2010, vol. 53, No. 1, pp. S388.
I. Jonassen et al., "Insulin Degludec: Multi-Hexamer Formation is the Underlying Basis for This New Generation Ultra-Long Acting Basal Insulin", Diabetologia, Sep. 2010, vol. 53, No. 1, pp. S388.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, Sep. 2010, vol. 53, No. 1, pp. S389.
Lane W. S. et al., High-dose insulin therapy: is it time for U-500 insulin?, Endocrine Practice, 2009, vol. 15, No. 1, pp. 71-79.
Segal A. R. et al., Use of concentrated insulin human regular (U-500) for patients with diabetes, American Journal of Health-System Pharmacy, 2010, vol. 67, No. 18, pp. 1526-1535.
Valentine V., Don't Resist Using U-500 Insulin and Pramlintide for Severe Insulin Resistance, Clinical Diabetes, 2012, vol. 30, No. 2, pp. 80-84.
Obesity Society: Your weight and diabetes—http://www.obesity.org/resources-for/your-weight-and-diabetes.htm, (accessed Jul. 21, 2015).
Inzucchi S. E. et al., Management of hyperglycaemia in type 2 diabetes: a patient-centered approach. Position statement of the American Diabetes Association (ADA) and the European Association for the Study of Diabetes (EASD), Diabetologia, 2012, vol. 55, No. 6, pp. 1577-1596.
Crasto W et al., Insulin U-500 in severe insulin resistance in type 2 diabetes mellitus, Postgraduate Medical Journal, 2009, vol. 85, No. 1002, pp. 219-222.
Heise T et al., Insulin Degludec Has a Two-Fold Longer Half-Life and a More Consistent Pharmacokinetic Profile Than Insulin Glargine, Diabetes, 2011, vol. 60(Suppl 1), LB11, (Abstract 37-LB).
Nosek L. et al., Ultra-Long-Acting Insulin Degludec Has a Flat and Stable Glucose-Lowering Effect, Diabetes 2011, 60(Suppl 1), LB14 (Abstract 49-LB).
Korsatko S. et al., Ultra-Long-Acting Insulin Degludec: Two Different Formulations (U100 and U200) Are Bioequivalent and Show Similar Pharmacodynamics, Diabetes 2011, 60(Suppl 1), A624 (Abstract 2349-PO).
Zinman B. et al., Insulin degludec, an ultra-long-acting basal insulin, once a day or three times a week versus insulin glargine once a day in patients with type 2 diabetes: a 16-week, randomized, open-label, phase 2 trial. The Lancet, 2011, vol. 377, 924-931.
Heller S. et al., Insulin degludec, an ultra-longacting basal insulin, versus insulin glargine in basal-bolus treatment with mealtime insulin aspart in type 1 diabetes (BEGIN Basal-Bolus Type 1): a phase 3, randomised, open-label, treat-to-target non-inferiority trial, The Lancet 2012, vol. 379, pp. 1489-1497.
Garber A. J. et al., Insulin degludec, an ultra-longacting basal insulin, versus insulin glargine in basal-bolus treatment with mealtime insulin aspart in type 2 diabetes (BEGIN Basal-Bolus Type 2): a phase 3, randomised, open-label, treat-to-target non-inferiority trial, The Lancet, 2012, vol. 379, pp. 1498-1507.
Declaration of Helsinki, Ethical principles for medical research involving human subjects., Journal of Indian Medical Association, 2009, vol. 107, No. 6, pp. 403-405.
Defining and Reporting Hypoglycemia in Diabetes: A report from the American Diabetes Association Workgroup on Hypoglycemia, Diabetes Care, 2005, vol. 28, No. 5, pp. 1245-1249.
Humulin® R Regular U-500 (Concentrated), Insulin Human Injection, USP (rDNA Origin), Eli Lilly and Company, Lilly USA, LLC, Indianapolis, IN 46285, USA.
Thornton S. et al., Intravenous overdose of insulin glargine without prolonged hypoglycemic effects, The Journal of Emergency Medicine, 2012, vol. 43, No. 3, pp. 435-437, XP002711646.
Zinman B. et al., Insulin degludec versus insulin glargine in insulin-naive patients with type 2 diabetes: a 1-year, randomized, treat-to-target trial (BEGIN Once long), Diabetes Care, 2012, vol. 35, No. 12, pp. 2464-2471, XP9172018.
Rodbard H et al., Reduced risk of hypoglycaemia with insulin degludec vs insulin glargine in patients with type 2 diabetes requiring high doses of basal insulin: meta-analysis of five randomized trials. Presented as an oral at the AACE 21st Annual Scientific and Clinical Congress, Philadelphia, PA, 2012, (Abstract 241).
ICH Harmonised Tripartite Guideline: Guideline for Good Clinical Practice, Journal of postgraduate medicine, 2001, vol. 47, No. 3, pp. 199-203.
Marcus A., Diabetes care—insulin delivery in a changing world, The Medscape Journal of Medicine, 2008, vol. 10, No. 5, 120.
Hoevelmann U. et al., Insulin degludec 200 U/ml is ultra-langacting and has a flat and stable glucose-lowering effect, Diabetologia, 2012, vol. 55, No. Suppl. 1, pp. S374-S375, XP002723769 & 48th Annual Meeting of the European-Association-for-the-Study-of-Diabetes; Berlin, Germany; Oct. 1-5, 2012.
Wang F. et al., Insulin degludec as an ultralong-acting basal insulin once a day: a systematic review, Diabetes, Metabolic Syndrome and Obesity: Targets and Therapy, 2012, vol. 5, pp. 191-204, XP002723770.
Korsatko S. et al., Ultra-long-acting insulin degludec: bioequivalence and similar pharmacodynamics shown for two different formulations (U100 and U200), Diabetologia, 2011, vol. 54, No. Suppl. 1, XP002723771, p. S427, & 47th Annual Meeting of the European-Association-for-the-Study-of-Diabetes (EASD); Lisbon, Portugal; Sep. 12-16, 2011.
Anthony H. Barnett, Diabetic Medicine, A Review of Basal Insulins, 2003, vol. 20, No. 11, pp. 873-885.
Heise, T. et al., Diabetes, Obesity and Metabolism, Towards Peakless, Reproducible and Long-Acting Insulins. An Assessment of the Basal Analogues Based on Isoglycaemic Clamp Studies, 2007, vol. 9, No. 5, pp. 648-659.
IDF Clinical Guidelines Task Force, Brussels: International Diabetes Federation 2005, Global Guideline for Type 2 Diabetes, 2005.
IDF Clinical Guidelines Task Force, Brussels: International Diabetes Federation 2007, Guideline for Management of Postmeal Glucose, 2007.
Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.
Talboys Catalog, 2008 Laboratory Equipment Catalog, Talboys by Troemner, 122 pages (2008).
Heise et al "Lower Within-Subject Variability of Insulin Detemir in Comparison to NPH Insulin an Insulin Glargine in People with Type 1 Diabetes" Diabetes, 2004, vol. 53, pp. 1614-1620.

(56) References Cited

OTHER PUBLICATIONS

Novo Nordisk, Levemir Product Information, Jun. 16, 2005. 42 pages.
Annual Review Endocrine Metabolism 2000, pp. 46-53.
"America Pink", http://america.pink/insulin-degludec_2091149.html, downloaded Aug. 24, 2016.
Heise et al., "Insulin Degludec 200 U/mL is Ultra-Long Acting and Has a Flat and Stable Glucose-Lowering Effect," Canadian Journal of Diabetes, 2012, vol. 36, No. 6, p. S13.
Springer et al., "Management of Type 2 Diabetes Mellitus in Children and Adolescents", Pediatrics, 2013, vol. 131, No. 2, pp. e648-e664.
Tambascia et al., "Degludec: the new ultra-long insulin analogue," Diabetology Metabol. Synd., 2015, vol. 7, pp. 1-7.

* cited by examiner

ADMINISTRATION REGIME

CROSS-REFERENCE TO RELATED APPLICATIONS

This application is a 35 U.S.C. § 371 National Stage application of International Application PCT/EP2014/058842 (published as WO 2014/177623), filed Apr. 30, 2014, which claimed priority of European Patent Applications 13166093.8, filed Apr. 30, 2013 and 13169312.9, filed May 27, 2013; this application claims priority under 35 U.S.C. § 119 of U.S. Provisional Applications 61/821,465, filed May 9, 2013 and 61/830,235, filed Jul. 22, 2013, the contents thereof which are incorporated by reference in their entirety.

FIELD OF THE INVENTION

The present invention relates to a novel administration regime useful in the treatment of diseases or conditions where administration of insulin will be of benefit, as well as to kits for use in the same.

BACKGROUND OF THE INVENTION

Diabetes mellitus (DM) is impaired insulin secretion and variable degrees of peripheral insulin resistance leading to hyperglycemia.

Years of poorly controlled hyperglycemia lead to multiple, primarily vascular complications that affect small vessels (microvascular), large vessels (macrovascular), or both. Indeed, diabetes mellitus is one of the major causes of premature morbidity and mortality.

The mechanisms by which vascular disease develops include glycosylation of serum and tissue proteins with formation of advanced glycation end products; superoxide production; activation of protein kinase C, a signalling molecule that increases vascular permeability and causes endothelial dysfunction; accelerated hexosamine biosynthetic and polyol pathways leading to sorbitol accumulation within tissues; hypertension and dyslipidemia that commonly accompany DM; arterial microthromboses; and proinflammatory and prothrombotic effects of hyperglycemia and hyperinsulinemia that impair vascular autoregulation. Immune dysfunction is another major complication and develops from the direct effects of hyperglycemia on cellular immunity.

Effective control of blood/plasma glucose can prevent or delay many of these complications but may not reverse them once established. Hence, achieving good glycemic control in efforts to prevent diabetes complications is the primary goal in the treatment of type 1 and type 2 diabetes.

Studies also support the role of glycated haemoglobin ($HbA_{1c}$) reduction in decreasing cardiovascular disease risk (Nathan D M, Cleary P A, Backlund J Y, et al. Intensive diabetes treatment and cardiovascular disease in patients with type 1 diabetes. N Engl J Med 2005; 353:2643-53; Selvin E, Marinopoulos S, Berkenblit G, et al. Meta-analysis: glycosylated hemoglobin and cardiovascular disease in diabetes mellitus. Ann Intern Med 2004; 141:421-31). The general goal of an $HbA_{1c}$ level of below 7% has been recommended by many diabetes organisations (e.g., the American Diabetes Association (ADA)). In the UKPDS, 50% of patients were taking insulin therapy to maintain $HbA_{1c}$ levels of below 7% within 6 years of the diagnosis of type 2 diabetes.

There are numerous non-insulin treatment options for diabetes, however, as the disease progresses, the most robust response will usually be with insulin. Indeed, since diabetes is associated with progressive β-cell loss, many patients, especially those with long-standing disease, will eventually need to be transitioned to insulin, since the degree of hyperglycemia (e.g., $HbA_{1c} \geq 8.5\%$) makes it unlikely that another drug will be of sufficient benefit.

Most patients express reluctance to beginning injectable therapy, due to discomfort and inconvenience caused by the high demands for blood glucose testing and insulin injection. Traditionally, the use of insulin to improve glycaemic control was provided by medical specialists. With the increasing number of patients under primary care for whom insulin is indicated, prescribing it in the same setting appears much more convenient for the end users. Often however, insulin is not started in time, due to psychological resistance from both doctors and patients.

A consensus statement from the American Diabetes Association (ADA) and the European Association for the Study of Diabetes (EASD) was updated in 2012, and emphasised a patient-centred approach and individualised HbA1c treatment targets for the management of hyperglycaemia in type 2 diabetes (T2DM). It recommended that insulin could be considered as one of the options for dual combination therapy, if an individualised HbA1c level target was not reached after metformin therapy. This choice could be based on patient and drug characteristics, with an over-riding goal of improving glycaemic control while minimising side-effects. When three-drug combinations are considered, insulin is likely to be more effective than most other agents (e.g., sulfonylurea, thiazolidinedione, dipeptidyl peptidase 4 inhibitor, glucagon-like peptide-1 receptor agonist), especially when the HbA1c level is very high ($\geq 9.0\%$) (Inzucchi S E, Bergenstal R M, Buse J B, et al., Management of hyperglycemia in type 2 diabetes: a patient-centered approach: position statement of the American Diabetes Association (ADA) and the European Association for the Study of Diabetes (EASD). Diabetes Care 2012; 35:1364-79).

The ideal insulin regimen aims to mimic the physiological profile of insulin secretion as closely as possible. There are two major components in the insulin profile: a continuous basal secretion and prandial surge after meals. The basal secretion controls overnight and fasting glucose while the prandial surges control postprandial hyperglycaemia.

Based on the time of onset and duration of their actions, injectable formulations can be broadly divided into basal (long-acting analogues [e.g., insulin detemir and insulin glargine] and ultra-long-acting analogues [e.g., insulin degludec]) and intermediate-acting insulin [e.g., isophane insulin] and prandial (rapid-acting analogues [e.g., insulin aspart, insulin glulisine and insulin lispro]). Premixed insulin formulations incorporate both basal and prandial insulin components.

There are various recommended insulin regimes, such as (1) multiple injection regimen: rapid-acting insulin before meals with long-acting insulin once or twice daily; (2) premixed analogues or human premixed insulin once or twice daily before meals; (3) intermediate- or long-acting insulin once or twice daily. However, where possible, a long-acting insulin regimen alone or in combination with oral antidiabetic drug(s) (OADs) is usually the optimal initial regimen for subjects with T2DM as this reduces the patient burden and discomfort caused by blood glucose measurement and injection of insulin.

Recent data from the United Kingdom Prospective Diabetes Study suggest the importance of stringent glycaemic control (Holman R R, Paul S K, Bethel M A, Matthews D R, Neil H A. 10-year follow-up of intensive glucose control in type 2 diabetes. N Engl J Med 2008; 359: 1577-1589) and current treatment guidelines call for early insulin treatment in type 2 diabetes patients (Nathan D M, Buse J B, Davidson M B et al. Management of hyperglycemia in type 2 diabetes: a consensus algorithm for the initiation and adjustment of therapy: update regarding thiazolidinediones: a consensus statement from the American Diabetes Association and the European Association for the Study of Diabetes. Diabetes Care 2008; 31: 173-175). However, optimal initiation and titration methods for the long-acting basal insulins are still being determined. Evidence suggests that many patients often do not have insulin doses titrated sufficiently to achieve target levels of glucose control (remaining on suboptimal doses and failing to reach treatment targets) (UK Prospective Diabetes Study (UKPDS) Group).

What has become increasingly clear is that patient empowerment is essential for motivation to reach treatment targets. Self-titration regimens facilitate empowerment of patients, allowing them to become more involved in their treatment, which can result in improved glycaemic control. Until recently, titration of insulin in type 2 diabetes clinical trials was typically left up to the investigator's discretion with a simple statement of the target ranges for glucose. In type 2 diabetes trials the average glycemic control achieved was usually less than desirable. Since then a number of trials have been conducted and reported utilizing various algorithms under various conditions.

During the last decade various insulin titration algorithms have been applied in several trials initiating long or intermediate acting insulin in type 2 diabetes patients often referred to as Treat-to-target. Several of the trials were designed for other primary purposes than algorithm development and have therefore used one specific algorithm. Interpretation of algorithm merit in those cases is somewhat difficult and has to rely on cross trial comparisons. Various factors in addition to the numbers in the algorithm apparently affect the achieved results.

The algorithms for basal insulin titration and their implementation have evolved steadily further away from complete real time health care provider control over every dose decision. The first step was the acceptance of one algorithm for all patients, which at the time was considered radical by most investigators. The second step became acceptance algorithm enforcement.

Controlled clinical trials such as the Diabetes Control and Complications Trial (The effect of intensive treatment of diabetes on the development and progression of long-term complications in insulin-dependent diabetes mellitus. The Diabetes Control and Complications Trial Research Group. N Engl J Med 1993; 329:977-86), the UK Prospective Diabetes Study (UKPDS) (Intensive blood-glucose control with sulphonylureas or insulin compared with conventional treatment and risk of complications in patients with type 2 diabetes (UKPDS 33), UK Prospective Diabetes Study (UKPDS) Group. Lancet 1998; 352:837-53), the Veterans Affairs Diabetes Trial (Duckworth W, Abraira C, Moritz T, et al. Glucose control and vascular complications in veterans with type 2 diabetes. N Engl J Med 2009; 360:129-39), the Action in Diabetes and Vascular Disease: Preterax and Diamicron Modified Release Controlled Evaluation trial (ADVANCE Collaborative Group, Patel A, MacMahon S, et al. Intensive blood glucose control and vascular outcomes in patients with type 2 diabetes. N Engl J Med 2008; 358: 2560-72), and a study on Japanese patients (Ohkubo Y, Kishikawa H, Araki E, et al. Intensive insulin therapy prevents the progression of diabetic microvascular complications in Japanese patients with non-insulin-dependent diabetes mellitus: a randomized prospective 6-year study. Diabetes Res Clin Pract 1995; 28:103-17) demonstrated that intensive glycaemic control could significantly reduce the risk of microvascular complications.

Common to all basal insulin titration algorithms is that dose changes are based on averages of a varying number of days' morning fasting self-monitored blood or plasma glucose. From this general theme there are many variations.

The starting dose has been 10 U, 20 U, or based on the morning fasting plasma glucose (FPG) using the formula of Holman and Turner (Holman R R, Turner R C. A practical guide to basal and prandial insulin therapy. Diabet Med. 1985 January; 2(1):45-53) which is (FPG (mg/dl)−50)/10, typically yielding just short of 20 U. Within these options there does not appear to be any difference in achieved glycemic control and hypoglycemia rate.

When a clinic has to titrate the insulin dose for the individual patient, there is often a natural limitation on the possible frequency. Consequently, the clinic has to be able to make substantial dose increments at high average glucose so the patient is not left for too long a time in poor glycemic control. However, the patient can easily titrate often, for which there is a long tradition for those with type 1 diabetes. With more frequent titration there may be a reduced need for large dose steps at high glucose levels and the algorithms can be simplified in terms of number of steps.

Earlier titration protocols typically titrated an insulin dose based on the average of a week's worth of several fasting blood/plasma measurements. Later trials are based on dose titrations based on average fasting blood/plasma measurements based of 3 measurements per week.

At the extreme is INSIGHT (Gerstein H C, Yale J F, Harris S B, Issa M, Stewart J A, Dempsey E. A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study. Diabet Med. 2006 July; 23(7):736-42), which has only one step of one unit of insulin titrated every morning by the patient.

Clinic contact initially occurred every other week, but after 4 weeks the clinic contact went to every 4 weeks and after 12 weeks to 6-week intervals. Clinic oversight was thus minimally if at all intensified compared to standard clinical practice. Patients were taught to "start with an initial dose of 10 units, and advised to increase this by 1 unit each day until achieving a FPG (FPG)≤5.5 mmol/liter (99 mg/dl)." The end insulin dose was 38 U and $HbA_{1c}$ 7.0%. From an effectiveness point of view, this is an "outstanding" result. Hence, there is a trend toward increasingly high frequency of insulin dose titration in order to improve to primary aim of insulin therapy—glycaemic control.

Diabetes care guidelines and product labelling for current basal insulin analogs recommend regular blood glucose self-measurement (American Diabetes Association. Standards of Medical Care in Diabetes—2012. Diabetes Care. 2012; 35(Suppl 1):S11-63; International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012; Canadian Diabetes Association Clinical Practice Guidelines Expert Committee. Canadian Diabetes Association. Can J Diabetes. 2008; 32(Suppl 1):S1-201; Meneghini L, Koenen C, Wenig W, Selam J-L. The usage of a simplified self-titration dosing guideline (303 Algorithm) for insulin detemir in patients with type 2 diabetes results of the randomized, controlled PREDICTIVE™ 303 study. Diabetes Obes Metab. 2007; 9:902-13; Davies M, Storms F, Shutler S, Bianchi-Biscay M, Gomis R. Improvement of glycemic control in subjects with poorly controlled type 2 diabetes. Diabetes Care. 2005; 28:1282-8; and LANTUS® (insulin glargine [rDNA origin] injection). Sanofi-aventis U.S. LLC, Bridgewater, N.J., USA; 2007. Health Care Professional. Dosing & Titration. Available at: http://www-.lantus.com/hcp/titration.aspx. Accessed Nov. 13, 2012) in order to help people with diabetes maintain appropriate glycemic control and become more actively involved in their healthcare (Benjamin E M. Self-monitoring of blood glucose: the basics. Clin Diabetes. 2002; 20(1):45-7; Schnell O, Saarlouis H A, Battelino T B, et al. Consensus statement on self-monitoring of blood glucose in diabetes. Diabetes, Stoffwechsel and Herz. 2009; 4:285-9; and American Diabetes Association. Insulin administration. Diabetes Care. 2012; 35:S1). Insulin dose is also typically determined and titrated up or down as needed according to algorithms based on blood glucose results (American Diabetes Association. Standards of Medical Care in Diabetes—2014. Diabetes Care. 2014; 37 Suppl 1). Insulin dose determination is individual for each patient. The dose steps (titration model), the glycemic target as well as the absolute insulin dose are determined in an individualised and tailored manner for each individual generally by a healthcare provider (HCP).

Challenges exist that can prevent the achievement of glycemic targets with insulin, including perceptions on the part of patients and HCPs that insulin therapy can be burdensome or too complex to manage (Peyrot M, Barnett A H, Meneghini L F, Schumm-Draeger P M. Factors associated with injection omission/non-adherence in the Global Attitudes of Patients and Physicians in Insulin Therapy Study. Diabetes Obes Metab. 2012; 14:1081-7; and Peyrot M, Barnett A H, Meneghini L F, Schumm-Draeger P M. Insulin adherence behaviours and barriers in the multinational Global Attitudes of Patients and Physicians in insulin therapy study. Diabet Med. 2012; 29:682-90). Patients who take an active role in the management of their diabetes and titration of their insulin may feel more empowered to take charge of their self-care and have a stronger belief that their actions can influence their disease, thus leading to better treatment outcomes (Norris S L, Lau J, Smith S J, et al. Self-management education for adults with type 2 diabetes: a meta-analysis on the effect of glycemic control. Diabetes Care. 2002; 25:1159-71; Kulzer B, Hermanns N, Reinecker H, Haak T. Effects of self-management training in type 2 diabetes: a randomized, prospective trial. Diabet Med. 2007; 24:415-23; Anderson R M, Funnell M M, Butler P M, et al. Patient empowerment: results of a randomized controlled trial. Diabetes Care. 1995; 18:943-9). In determining how self-care can best be facilitated for patients with diabetes, the cost and burden of frequent glucose testing must be considered when designing treatment plans, as these can be significant factors when added to the health, quality of life (QoL), and financial toll of poorly controlled diabetes.

Numerous studies investigating the cost of self-measured blood glucose (SMBG) testing have found that it comprises a substantial portion of diabetes-related expenditures (Liebl A, Breitscheidel L, Nicolay C, Happich M. Direct costs and health-related resource utilisation in the 6 months after insulin initiation in German patients with type 2 diabetes mellitus in 2006: INSTIGATE study. Curr Med Res Opin. 2008; 24:2349-58; Yeaw J, Christensen T E, Groleau D, Wolden M L, Lee W C. Self-monitoring blood glucose test strip utilization in Canada. Diabetes. 2012; 61(Suppl 1):A35; Yeaw J, Lee W C, Wolden M L, Christensen T, Groleau D. Cost of self-monitoring of blood glucose in Canada among patients on an insulin regimen for diabetes. Diabetes Ther. Epub Jun. 27, 2012. doi: 10.1007/s13300-012-0007-6; and Yeaw J, Lee W C, Aagren M, Christensen T J. Cost of self-monitoring of blood glucose in the United States among patients on an insulin regimen for diabetes. J Manag Care Pharm. 2012; 18:21-32). In a retrospective database analysis in the US that included more than 45,000 patients, testing accounted for 27% of diabetes care costs: total combined blood glucose testing and insulin-related costs were $2,850 USD/patient/year, with $772 USD/patient/year attributed to blood glucose testing alone (Yeaw J, Lee W C, Aagren M, Christensen T J. Cost of self-monitoring of blood glucose in the United States among patients on an insulin regimen for diabetes. J Manag Care Pharm. 2012; 18:21-32). In other countries, testing comprises an even higher percentage of diabetes care costs, e.g., 40% in Canada (Yeaw J, Christensen T E, Groleau D, Wolden M L, Lee W C. Self-monitoring blood glucose test strip utilization in Canada. Diabetes. 2012; 61(Suppl 1):A35; Yeaw J, Lee W C, Wolden M L, Christensen T, Groleau D. Cost of self-monitoring of blood glucose in Canada among patients on an insulin regimen for diabetes. Diabetes Ther. Epub Jun. 27, 2012. doi: 10.1007/s13300-012-0007-6) and 42% in Germany (Liebl A, Breitscheidel L, Nicolay C, Happich M. Direct costs and health-related resource utilisation in the 6 months after insulin initiation in German patients with type 2 diabetes mellitus in 2006: INSTIGATE study. Curr Med Res Opin. 2008; 24:2349-58).

Hence, there is pressure to reduce the frequency of blood glucose measurement in order to improve patient quality of life, improve administration regime adherence (leading to improved patient outcomes) and reduce treatment costs. However, there are conflicting pressures to increase the frequency of blood glucose measurement and insulin administration in order to most effectively achieve glycemic control and thereby reduce diabetes-associated complications.

Accordingly, there is an ongoing need to provide improved approaches for long- and ultra-long-acting insulin dosing and administration.

DESCRIPTION OF THE INVENTION

It is well established that the risk of microvascular and macrovascular complications is related to glycemia, as measured by $HbA_{1c}$ (glycosylated hemoglobin)—the levels of which reflect the glycemia levels of the subject of the previous 2-3 months.

Obtaining target $HbA_{1c}$ levels remains a major focus of therapy (see, for example, Stratton, et al., 2000.).

The ADA's "Standards of Medical Care in Diabetes" recommends lowering $HbA_{1c}$ to <7.0% in most patients to reduce the incidence of microvascular disease. This can be achieved with a mean plasma glucose of ~8.3-8.9 mmol/L (~150-160 mg/dL); ideally, fasting and pre-meal glucose should be maintained at <7.2 mmol/L (<130 mg/dL) and the postprandial glucose at <10 mmol/L (<180 mg/dL). More stringent HbA1c targets (e.g., 6.0-6.5%) might be considered in selected patients (with short disease duration, long life expectancy, no significant cardiovascular disease) if this can be achieved without significant hypoglycaemia or other adverse effects of treatment. Conversely, less stringent HbA$_{1c}$ goals, e.g., 7.5-8.0% or even slightly higher are appropriate for patients with a history of severe hypoglycemia, limited life expectancy, advanced complications, extensive comorbid conditions and those in whom the target is difficult to attain despite intensive self-management education, repeated counselling, and effective doses of multiple glucose-lowering agents, including insulin.

The present inventors have surprisingly found that long-acting insulin can be titrated based on a single fasting blood (or plasma) glucose measurement with similar improvements to HbA$_{1c}$ levels found with traditional titration methods based on three consecutive fasting blood glucose measurements.

This simplified regime allows a patient-focused titration algorithm that would encourage self-titration, enhancing patient empowerment as well as substantially reducing treatment costs by reducing the frequency of blood glucose measurements required for dose adjustments without reducing therapeutic outcomes.

Accordingly, a first aspect of the present invention provides a long-acting insulin for use in treating a disease or condition where administration of insulin will be of benefit, wherein the administration of the long-acting insulin comprises or consists of the following steps:
(a) optionally providing a fasting blood sample to be tested from an individual in need of treatment;
(b) taking a single fasting blood (or plasma) glucose measurement from an individual in need of treatment;
(c) using the single fasting blood (or plasma) glucose measurement to determine the long-acting insulin dose to be administered; and
(d) administering the long-acting insulin to the individual at the dose determined in step (c).

Hence, in the present invention, long-acting insulin dosage is not determined or titrated using an average of (and/or selection from) a plurality of blood glucose/plasma measurements. Rather, long-acting insulin dosage is determined or titrated based on a single blood/plasma glucose measurement.

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

An "insulin" or "naturally occurring insulin" according to the invention is herein to be understood as human insulin or an insulin from another species such as porcine or bovine insulin.

The term "insulin peptide" as used herein means a peptide which is either human insulin or an analog or a derivative thereof with insulin activity.

The term "parent insulin" as used herein is intended to mean an insulin before any modifications have been applied thereto.

The term "insulin analogue" as used herein means a modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modification relative to human insulin.

Modifications in the insulin molecule are denoted stating the chain (A or B), the position, and the one or three letter code for the amino acid residue substituting the native amino acid residue.

By "desB30" or "B(1-29)" is meant a natural insulin B chain or an analogue thereof lacking the B30 amino acid and "A(1-21)" means the natural insulin A chain. Thus, e.g., A21Gly,B28Asp,desB30 human insulin is an analogue of human insulin where the amino acid in position 21 in the A chain is substituted with glycine, the amino acid in position 28 in the B chain is substituted with aspartic acid, and the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21 Gln, respectively.

Herein the terms "A(0)" or "B(0)" indicate the positions of the amino acids N-terminally to A1 or B1, respectively. The terms A(−1) or B(−1) indicate the positions of the first amino acids N-terminally to A(0) or B(0), respectively. Thus A(−2) and B(−2) indicate positions of the amino acids N-terminally to A(−1) and B(−1), respectively, A(−3) and B(−3) indicate positions of the amino acids N-terminally to A(−2) and B(−2), respectively, and so forth. The terms A22 or B31 indicate the positions of the amino acids C-terminally to A21 or B30, respectively. The terms A23 or B32 indicate the positions of the first amino acids C-terminally to A22 or B31, respectively. Thus A24 and B33 indicate positions of the amino acids C-terminally to A23 and B32, respectively, and so forth.

Herein, the term "amino acid residue" is an amino acid from which, formally, a hydroxy group has been removed from a carboxy group and/or from which, formally, a hydrogen atom has been removed from an amino group.

Examples of insulin analogues are such wherein Pro in position 28 of the B chain is substituted with Asp, Lys, Leu, Val, or Ala and/or Lys at position B29 is substituted with Pro, Glu or Asp. Furthermore, Asn at position B3 may be substituted with Thr, Lys, Gln, Glu or Asp. The amino acid residue in position A21 may be substituted with Gly. Also one or more amino acids may be added to the C-terminal of the A-chain and/or B-chain such as, e.g., Lys. The amino acid in position B1 may be substituted with Glu. The amino acid in position B16 may be substituted with Glu or His. Further examples of insulin analogues are the deletion analogues, e.g., analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

By 'long-acting insulin' we include a derivative or analogue of a naturally occurring insulin that:
(a) exhibits in physiological conditions, at least in part, the insulin receptor binding of the naturally occurring insulin, preferably, at least 0.01% of the insulin receptor binding of the naturally occurring insulin, for example, at least 0.1%, at least, 1%, at least 5%, at least 10%, at least 15%, at least 20%, at least 25% at least 50%, at least 65%, at least 75%, at least 85%, at least 95%, at least 100%, at least 110%, at least 120%, at least 130%, at least 140% or at least 150% of the insulin receptor binding of the naturally occurring insulin, and/or, at least in part, the potency of the naturally occurring insulin, preferably, at least 25% of the potency of the naturally occurring insulin, for example, at least 50%, at least 65%, at least 75%, at least 85%, at least 95%, at least 100%, at least 110%, at least 120%, at least 130%, at least 140% or at least 150% of the potency of the naturally occurring insulin; and
(b) exhibits a mean terminal half life of at least 5 hours and less than 18 hours in physiological conditions when injected subcutaneously, for example, at least 7 hours, at least 8 hours, at least 10 hours, at least 12.5 hours, greater than 12.5 hours, at least 15 hours or at least 17.5 hours and less than 18 hours, between 5 and 17.5 hours, between 10 and 17.5 hours or between 15 and 17.5 hours.

Preferably, the 'long-acting insulin' also:
(c) induces in a subject a maximum deviation from mean insulin concentration (AUCF %) over a 24 hour period of $\leq\pm20$, for example $\leq\pm18$, $\leq\pm17$, $\leq\pm16$, $\leq\pm15$, $\leq\pm14$, $\leq\pm13$, $\leq\pm12$, $\leq\pm11$, $\leq\pm10$, $\leq\pm9$, $\leq\pm8$, $\leq\pm7$, $\leq\pm6$, $\leq\pm5$, $\leq\pm4$, $\leq\pm3$, $\leq\pm2$, $\leq\pm1$, $\leq\pm0.5$, $\leq\pm0.1$.

By 'ultra-long-acting' insulin we include a derivative or analogue of a naturally occurring insulin that:
(a) exhibits in physiological conditions, at least in part, the insulin receptor binding of the naturally occurring insulin, preferably, at least 0.01% of the insulin receptor binding of the naturally occurring insulin, for example, at least 0.1%, at least, 1%, at least 5%, at least 10%, at least 15%, at least 20%, at least 25% at least 50%, at least 65%, at least 75%, at least 85%, at least 95%, at least 100%, at least 110%, at least 120%, at least 130%, at least 140% or at least 150% of the insulin receptor binding of the naturally occurring insulin, and/or, at least in part, the potency of the naturally occurring insulin, preferably, at least 25% of the potency of the naturally occurring insulin, for example, at least 50%, at least 65%, at least 75%, at least 85%, at least 95%, at least 100%, at least 110%, at least 120%, at least 130%, at least 140% or at least 150% of the potency of the naturally occurring insulin;
(b) exhibits a mean terminal half life of at least 18 hr in physiological conditions when injected subcutaneously, for example, greater than 18 hours, at least 20 hours, greater than 20 hours, greater than 22 hours, at least 22.5 hours, or greater than 24 hours, at least 25 hours, at least 27.5 hours, at least 30 hours, at least 32.5, at least 35 hours, at least 37.5 hours, or at least 40 hours, or between 18 and 40 hours, between 20 and 40 hours, between 24 and 40 hours.

Preferably, the 'ultra-long acting insulin' also:
(c) induces in a subject a maximum deviation from mean insulin concentration (AUCF %) over a 24 hour period of $\leq\pm20$, for example, $\leq\pm18$, $\leq\pm17$, $\leq\pm16$, $\leq\pm15$, $\leq\pm14$, $\leq\pm13$, $\leq\pm12$, $\leq\pm11$, $\leq\pm10$, $\leq\pm9$, $\leq\pm8$, $\leq\pm7$, $\leq\pm6$, $\leq\pm5$, $\leq\pm4$, $\leq\pm3$, $\leq\pm2$, $\leq\pm1$, $\leq\pm0.5$, $\leq\pm0.1$.

In principle, the longer the half-life of the insulin, the more stable and evenly distributed the glucose-lowering effect over a dosing interval (i.e. time interval between injections).

In one embodiment, the long-acting insulin or the ultra-long-acting insulin, preferably the ultra-long acting insulin, provides a stable and evenly distributed glucose-lowering effect over a dosing interval. For example, the long acting or ultra-long acting insulin provides a glucose infusion rate (GIR) over a 24-h dosing interval (tau) quantified by estimating the ratio of AUC for sub-areas under the GIR profiles for all four 6-hour measurement intervals (proportion of GIR AUC: $AUC_{GIR,0-6h,SS}/AUC_{GIR,\tau,SS}$; $AUC_{GIR,6-12h,SS}/AUC_{GIR,\tau,SS}$, $AUC_{GIR,12-18h,SS}/AUC_{GIR,\tau,SS}$; $AUC_{GIR,18-24h,SS}/AUC_{GIR,\tau,SS}$) of about 25:25:25:25% distribution, preferably ±8%, for example, ±4%, ±3%, ±2%, ±1%, ±0.5% or ±0.1%. In one embodiment GIR distribution is evaluated according to the method described in Heise et al., 2012, *Diabetes, Obesity and Metabolism*, 14(10):944-50.

In one embodiment, the ultra-long-acting insulin provides a fluctuation in GIR across a dosing interval of 24 hours, evaluated by $AUCF_{GIR,\tau}$ (the mean fluctuation in GIR profile), of a $AUCF_{GIR,\tau} \leq 0.35$ mg/kg/min for an insulin dose of 0.4 U/kg, $\leq 0.50$ mg/kg/min for an insulin dose of 0.6 U/kg and/or $\leq 0.60$ or $\leq 0.50$ mg/kg/min for an insulin dose of 0.8 U/kg, or of a $AUCF_{GIR,\tau} \leq 0.30$ mg/kg/min for an insulin dose of 0.4 U/kg, $\leq 0.40$ mg/kg/min for an insulin dose of 0.6 U/kg and/or $\leq 0.45$ mg/kg/min for an insulin dose of 0.8 U/kg.

In another embodiment, the long-acting insulin provides a fluctuation in GIR across a dosing interval of 24 hours of a $AUCF_{GIR,\tau} \leq 0.40$ or $\leq 0.45$ mg/kg/min for an insulin dose of 0.4 U/kg, $\leq 0.60$ mg/kg/min for an insulin dose of 0.6 U/kg and/or $\leq 0.80$ mg/kg/min for an insulin dose of 0.8 U/kg.

$AUCF_{GIR,\tau}$ estimates how much an individual's GIR profile deviates from his/her mean GIR over 24 hours. Fluctuation in GIR ($AUCF_{GIR,\tau}$) can be evaluated by any suitable method known in the art. In one embodiment GIR fluctuation ($AUCF_{GIR,\tau}$) is evaluated according to the method described in Heise et al., 2012, *Diabetes, Obesity and Metabolism*, 14(9):859-64. See also for example, Heise et al., Poster EASD 2011 (Abstract 1046); or Heise et al., Poster ADA 2011 entitled "Insulin degludec has a two-fold longer half-life and a more consistent pharmacokinetic profile that insulin glargine" (Abstract 37-LB). These references also provide the GIR fluctuation figures for insulin degludec and for insulin glargine, as reported in Table 1.

By 'intermediate-acting insulin' we include a derivative or analogue of a naturally occurring insulin that:
(a) exhibits in physiological conditions, at least in part, the insulin receptor binding and/the potency of the naturally occurring insulin as defined herein in relation to a long acting insulin;
(b) exhibits a mean terminal half life of greater than 1.5 hr and less than 5 hours in physiological conditions when injected subcutaneously, for example, greater than 2 hr, greater than 2.5 hr, greater than 3 hr, greater than 3.5 hr, greater than 4 hr, greater than 4.5 hr and less than 5 hr.

By 'rapid-acting insulin' we include a derivative or analogue of a naturally occurring insulin that:
(a) exhibits in physiological conditions, at least in part, the insulin receptor binding of the naturally occurring insulin and/the potency of the naturally occurring insulin as defined herein in relation to a long acting insulin; and
(b) exhibits a mean terminal half life of less than 90 min in physiological conditions when injected subcutaneously, preferably less than or equal to 84 min, less than or equal to 78 min, less than or equal to 72 min, less than or equal to 66 min, less than or equal to 60 min, less than or equal to 54 min, less than or equal to 46 min, less than or equal to 42 min, less than or equal to 36 min, less than or equal to 30 min, less than or equal to 24 min, less than or equal to 18 min, less than or equal to 12 min, less than or equal to 6 min, less than or equal to 2.5 min or less than or equal to 1 min.

Insulin receptor binding may be determined by any suitable means known in the art. However preferably, insulin receptor binding is determined using the method provided in the foregoing examples (assay (I)—Insulin receptor binding).

Insulin potency may be determined by any suitable means known in the art. However preferably, insulin potency is determined using the method provided in the foregoing examples (assay (II)—Potency).

Insulin mean terminal half life may be determined by any suitable means known in the art, for example, see Heise T, Nosek L, Bøttcher S G, Hastrup H, Haahr H, 2012, 'Ultra-long-acting insulin degludec has a flat and stable glucose-lowering effect in type 2 diabetes' *Diabetes Obes Metab.*, 14(10):944-50, the disclosures of which are incorporated herein by reference. Insulin mean terminal half-life may alternatively be determined using the method provided in WO2005/012347 (assay (III).

Maximum deviation from mean insulin concentration (AUCF %) may be determined by any suitable means known in the art (see, for example, Heise et al., Poster EASD 2011; or Heise et al., Poster ADA 2011 entitled "Insulin degludec has a two-fold longer half-life and a more consistent pharmacokinetic profile that insulin glargine" *Diabetes* 2011: 60(Suppl 1):LB11 (Abstract 37-LB); or Heise et al., 2012, *Diabetes, Obesity and Metabolism,* 14(10):944-50).

Human insulin has three primary amino groups: the N-terminal group of the A-chain and of the B-chain and the ε-amino group of $Lys^{B29}$. Several insulin derivatives which are substituted in one or more of these groups are known in the prior art.

In addition, long acting insulin compositions are known in the art. One main type of long acting insulin compositions comprises injectable aqueous suspensions of insulin crystals or amorphous insulin. In these compositions, the insulin compounds utilized typically are protamine insulin, zinc insulin or protamine zinc insulin.

WO 2005/012347 (Novo Nordisk A/S) discloses acylated insulin derivatives comprising additional negatively charge compared to the acylated insulins disclosed in WO 95/07931. The pharmaceutical formulation of these acylated insulins are given as 2, 3 or 4 zinc atoms per hexamer insulin.

WO 2010/049488 discloses an insulin derivative for the treatment of a condition or disease where administration of insulin will be of benefit, comprising administering, to a patient in need thereof, effective dosages of the insulin derivative, wherein said insulin derivative exhibits a prolonged profile of action and wherein said dosages are administered at intervals longer than 24 hours.

According to the present invention, the basal insulin comprises or consists of long-acting insulin and ultra-long acting insulin.

According to the present invention, the basal insulin is administered in an amount to achieve a beneficial glycaemic control in said subject.

According to the present invention, the beneficial glycaemic control in said subject is determined by at least the levels of $HbA_{1c}$ (glycosylated haemoglobin) in said subject after administration of said basal insulin.

By use of the basal insulin and its administration according to the present invention it is possible to achieve improvements in the proportion of patients in need thereof reaching $HbA_{1c}$ targets.

Fasting blood glucose measurements are typically converted to fasting plasma glucose measurements using standard formulae (typically by multiplying the fasting blood glucose figure obtained by 1.11). Fasting blood or plasma glucose measurements may be taken using any suitable method known in the art. However, preferably, fasting blood/plasma glucose samples are assayed using a hexokinase-UV method. More preferably, fasting blood/plasma glucose is performed using a lancet and a glucose monitor for self measurement of blood glucose (SMBG) glucose by the patient. For more information on SMBG see Benjamin, 2002, 'Self-Monitoring of Blood Glucose: The Basics' *Clinical Diabetes;* 20(1):45-47 which is incorporated by reference herein.

Preferably the sample provided is a fasting blood sample (preferably a capillary blood sample) but equally, the fasting blood sample provided may be a plasma sample.

When using blood glucose meters the measurement is preferably performed with capillary blood calibrated to plasma equivalent glucose values i.e. the measurement is performed on blood while the value is reported as plasma.

Preferably the fasting blood/plasma glucose measurement is taken at the same time on each day of measurement (or within ±5 hours of that time, for example, within ±4.5 hours, within ±4 hours, within ±3.5 hours, within ±3 hours, within ±2.5 hours, within ±2 hours, within ±1.5 hours, within ±1 hour, ±45 min, ±30 min, ±15 min, ±10 min, ±5 min or ±1 min if that time). Preferably, the fasting blood/glucose measurement is taken at least 8 hours after eating (most preferably at least 9, 10, 11 or 12 hours after eating). Preferably, the fasting blood/glucose measurement is taken before breakfast.

By the term "individual" is meant a human. Preferably, the individual is an adult individual.

A second aspect of the invention provides a method of treating a disease or condition where administration of insulin will be of benefit, comprising or consisting of the following steps:
(a) (optionally) providing a fasting blood sample to be tested from an individual in need of treatment;

(b) taking a single fasting blood (or plasma) glucose measurement from an individual in need of treatment;
(c) using the single fasting blood (or plasma) glucose measurement to determine a long-acting or ultra-long-acting insulin dose to be administered; and
(d) administering said long-acting or ultra-long-acting insulin to the individual at the dose determined in step (c).

A third aspect of the invention provides a method of determining a long-acting or ultra-long-acting insulin dose to be administered to an individual suffering from a disease or condition where administration of insulin will be of benefit comprising or consisting of the following steps:
(a) optionally providing a fasting blood sample to be tested from an individual in need of treatment;
(b) taking a single fasting blood or plasma glucose measurement from said individual in need of treatment; and
(c) using the single fasting blood or plasma glucose measurement to determine the long-acting or ultra-long-acting insulin dose to be administered.

References herein to step (d) in respect of the third aspect of the invention do not refer to a literal step in the claimed method, but rather, to an administration step performed subsequent to the method of the third aspect, for which the dosage is determined in step (c).

A fourth aspect of the invention provides a kit for use of a long-acting or ultra-long-acting insulin as of first aspect of the invention, a method of treating a disease or condition as of second aspect of the invention or a method of determining an insulin dose as of third aspect of the invention, comprising or consisting of one or more of the following:
A) apparatus for providing a blood sample to be tested from an individual in need of treatment;
B) apparatus for measuring fasting blood glucose;
C) a long-acting or ultra-long-acting insulin;
D) one or more drug used in the treatment of diabetes; and/or
E) instructions for performing the use of a long-acting insulin as of first aspect of the invention, a method of treating a disease or condition as of second aspect of the invention or a method of determining an insulin dose as of third aspect of the invention.

The long-acting or ultra-long-acting insulin may be administered (or, in respect of aspect three, be for administration) at various frequencies based on a single blood glucose measurement. In one embodiment of the first, second or third aspects of the invention, in step (d), the long-acting insulin is administered (or to be administered) once, or at least once, every 72 hours, for example, the long-acting insulin may be administered once, or at least once, every 64 hours; once, or at least once, every 56 hours; once, or at least once, every 48 hours; once, or at least once, every 42 hours; once, or at least once, every 40 hours; once, or at least once, every 36 hours; once, or at least once, every 32 hours; once, or at least once, every 30 hours; once, or at least once, every 24 hours; once, or at least once, every 18 hours; once, or at least once, every 16 hours; or the long-acting or ultra-long-acting insulin is administered once, or at least once, every 8 hours.

In an alternative or additional embodiment of the first, second or third aspects of the invention, in step (d), the long-acting or ultra-long-acting insulin is administered (or to be administered) once, or at least once, every 8 to 72 hours, for example, once, or at least once, every 64 to 8 hours; once, or at least once, every 56 to 8 hours; once, or at least once, every 48 to 8 hours; once, or at least once, every 40 to 8 hours; once, or at least once, every 36 to 8 hours; once, or at least once, every 32 to 16 hours; once, or at least once, every 28 to 20 hours; once, or at least once, every 26 to 22 hours; once, or at least once, every 24 to 8 hours; once, or at least once, every 20 to 8 hours; or said insulin is administered once, or at least once, every 16 to 8 hours.

In an alternative or additional embodiment, in step (d), the long-acting or ultra-long-acting insulin is administered (or to be administered) once, or at least once, every 40 to 8 hours (preferably, once every 40 to 8 hours). In an alternative or additional embodiment, the long-acting or ultra-long-acting insulin is insulin degludec and, in step (d), said insulin is administered (or to be administered) once, or at least once, every 40 to 8 hours (preferably, once every 40 to 8 hours).

In an alternative or additional embodiment, in step (d), the long-acting or ultra-long-acting insulin is administered (or to be administered) once, or at least once, every 28 to 20 hours (preferably, once every 28 to 20 hours).

In an alternative or additional embodiment, in step (d), the long-acting or ultra-long-acting insulin is administered (or to be administered) once, or at least once, every 24 hours (preferably, once every 24 hours).

As well as being provided at a range of frequencies, the long-acting or ultra-long-acting insulin may be administered for various time periods based upon a dosage determined from a single blood glucose measurement (the administration period).

Hence, in an alternative or additional embodiment of the first, second or third aspects of the invention, step (d) is performed (or is to be performed) for an administration period of, or at least of, 1 day; for example, of, or at least of, 2 days; of, or at least of, 3 days; of, or at least of, 4 days; of, or at least of, 5 days; of, or at least of, 6 days; of, or at least of, 7 days; of, or at least of, 8 days; of, or at least of, 9 days; of, or at least of, 10 days; of, or at least of, 11 days; of, or at least of, 12 days; of, or at least of, 13 days; of, or at least of, 14 days or for an administration period of, or at least of, 15 days.

By 'administration period' we mean the period for which the long-acting or ultra-long-acting insulin is administered in a given dose as determined based on the latest single blood glucose measurement. Hence, the long-acting or ultra-long-acting insulin may be administered at a frequency of (for example) once every 24 hours for an administration period of (for example) 7 days. In this event, said insulin would be administered once per day during 7 days at a given dose, after which a further blood glucose measurement would be taken (i.e., step (b)), a further dose to be administered would be determined (i.e., step (c)), and a further dose of said insulin would be administered to the individual for a particular frequency and for a particular administration period (in this example, once per day, for 7 days) (i.e., step (d)) and so on. In this example, the administration period is a period of 7 days between two consecutive titrations.

Accordingly, in an alternative or additional embodiment of the first, second or third aspects of the invention, step (d) is performed for an administration period of between 1 and 15 days, for example, between 1 and 13 days; between 2 and 12 days; between 3 and 11 days; between 4 and 10 days; between 5 and 9 days; or for an administration period of between 6 and 8 days. Preferably step (d) is performed for an administration period of, or at least of, 7 days. More preferably, step (d) is performed for an administration period of 7 days. More preferably, step (d) is performed for an administration period of 7 days and the insulin is insulin degludec.

Since diseases or conditions where administration of insulin will be of benefit (such as diabetes mellitus) are generally chronic, it is generally necessary to repeat steps (a) to (d) of the first, second or third aspects of the invention. Hence, in an alternative or additional embodiment of the first, second or third aspects the invention comprises or consists of steps (a) to (d) and the following step(s):

(e) repeating steps (a) to (d).

Preferably, step (a) to (d) are repeated for as long as necessary and generally this will be continuous repetition.

Administration periods may be fixed i.e., may be for the same duration for each repetition of steps (a) to (d). However, fasting blood glucose levels may be stable in individuals having stable consumption and activity levels. In such individuals, less frequent adjustment of long-acting insulin dose may be required once a target fasting blood glucose level has been achieved, further reducing the testing burden on the user in terms of discomfort, inconvenience and cost.

Thus, in an alternative or additional embodiment of the first, second or third aspects of the invention, in step (e), steps (a) to (d) are repeated continuously and:

(i) the administration period of each step (d) is of the same duration or same range of duration in each repetition of steps (a) to (d); or (ii) the administration period of each step (d) is of the same duration or same range of duration in each repetition of steps (a) to (d) until a target fasting blood glucose level is achieved in the individual in need of treatment, after which, the duration or range of duration of the administration period of step (d) in subsequent repetitions of steps (a) to (d) is increased.

Although there may be gaps between repetitions of steps (a) to (d) it is preferred that in step (e), steps (a) to (d) are repeated contiguously (i.e., that each administration period directly follows the preceding administration period).

By 'target fasting blood glucose level' we include any target fasting blood glucose level deemed appropriate for a particular patient. Insulin therapies may be highly individual and hence, target fasting blood glucose levels may vary between individuals and between treatment regimes. However, in one alternative or additional embodiment, the target fasting blood or plasma glucose level is 4 to 5 mmol/L (71 to 90 mg/dL).

In an alternative or additional embodiment of the first, second or third aspects of the invention, in step (e)(ii), once the target blood glucose level is achieved in the individual in need of treatment, step (d) is then performed for an administration period of, or at least of, 2 weeks; for example, for an administration period of, or at least of, 3 weeks. Preferably, step (d) is then performed for an administration period of 2 weeks or 3 weeks.

Before increasing the duration of the administration period, it may be preferable to achieve the target fasting blood glucose level for two or more consecutive repetitions of steps (a) to (d) (to ensure that a fasting blood that is sufficiently stable to justify increasing the administration period has been achieved).

Hence, in an alternative or additional embodiment of the first, second or third aspects of the invention, in step (e)(ii) steps (a) to (d) are repeated continuously until the target blood glucose level is achieved in 1, or at least 1, step (b), for example, 2, or at least 2, consecutive repetitions of step (b); 3, or at least 3, consecutive repetitions of step (b); 4, or at least 4, consecutive repetitions of step (b); 5, or at least 5, consecutive repetitions of step (b); 6, or at least 6, consecutive repetitions of step (b); 7, or at least 7, consecutive repetitions of step (b); 8, or at least 8, consecutive repetitions of step (b); 9, or at least 9, consecutive repetitions of step (b); 10, or at least 10, consecutive repetitions of step (b).

To determine insulin dose in titration step (c), an individual would add or subtract a number of units of insulin based on the blood glucose measurement. This dose adjustment is individual and follows recommendations tailored for each individual generally by a HCP. It also depends on the glycemic target which is also individual and adjusted by a HCP to each individual's need.

Insulin dose may be determined through a variety of methods, for example, may be calculated based on weight (and/or height), fasting blood glucose and gender (thereafter adjusted empirically according to fast blood glucose and/or $HbA_{1c}$ level outcome). It is increasingly common to use a titration method wherein, after administering an initial dose standard or empirically-determined dose, further doses are adjusted by pre-determined increments (e.g. titration algorithm), as necessary, based on blood glucose/plasma measurements in order to reach and maintain a target blood glucose/plasma and/or $HbA_{1c}$ level. Such titration models are however always given as guidance only and individual adjustments are applicable on a case by case basis.

Hence, in an alternative or additional embodiment of the first, second or third aspects of the invention in step (c), the long-acting or ultra-long-acting insulin dose to be administered is determined using titration.

In an alternative or additional embodiment of the first, second or third aspects of the invention, in step (b), the single fasting blood (or plasma) glucose measurement is performed using a self-measurement blood glucose (SMBG) test.

In an alternative or additional embodiment of the first, second or third aspects of the invention, prior to step (a) (where present) and step (b), the initial insulin is administered in a first administration period at a predetermined dose (i.e., a dose not based on blood or plasma glucose levels, but rather, based on a preferred starting point for insulin titration).

In an alternative or additional embodiment of the first, second or third aspects of the invention, prior to step (a) (where present) and step (b), the initial insulin is administered in a first administration period at a dose of 10 U.

As used herein the term "U" refers to a unit of insulin (or an analogue or derivative thereof). The designation "U" with a number following indicates the concentration as measured by the number of units per ml of fluid volume (Joslin's Diabetes Deskbook, 2nd edition, Chapter 9 Using insulin to treat diabetes—general principles, page 268). Further information about the meaning of "U" can be found in a document from the EMA (reference EMEA/CHMP/BWP/124446/2005) entitled "Guideline on potency labelling for insulin analogue containing products with particular reference to the use of "International Units" or "Units"" (see http://www.ema.europa.eu/docs/en_GB/document_library/Scientific_guideline/2009/09/WC500003654.pdf). "IU" refers to an international unit of human insulin as defined according to the WHO Expert Committee on Biological Standardization. IU is a standardized parameter. For commercial insulins, the labels indicate the content of 1 U (unit) of the particular insulin analogue.

In an alternative or additional embodiment of the first, second or third aspects of the invention, in step (b), where the single blood or plasma glucose measurement taken from the individual in need of treatment in step (c) is a plasma glucose measurement of:

≤3.9 mmol/L (≤70 mg/dL): the dose administered in step (d) is reduced by 4 U compared to the dose previously administered;

4 to 5 mmol/L (71 to 90 mg/dL): the dose administered in step (d) is unaltered compared to the dose previously administered; and ≥5.1 mmol/L (≥91 mg/dL): the dose administered in step (d) is increased by 4 U compared to the dose previously administered.

In an alternative or additional embodiment of the first, second, third or fourth aspects of the invention the long-acting or ultra-long acting insulin, preferably the ultra-long acting insulin, is any one or more of the compounds disclosed in WO 2005/012347, which are incorporated herein by reference. In some instances, these compounds are referred as being "the '347 derivatives".

Hence, in an alternative or additional embodiment of the first, second, third or fourth aspects of the invention the long-acting or ultra-long-acting insulin, preferably the ultra-long acting insulin, has a side chain attached to the α-amino group of the N-terminal amino acid residue of the B chain or to the ε-amino group of the Lys residue present in the B chain of the parent insulin, the side chain being of the general formula:

—W—X—Y—Z wherein W is:
(i) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
(ii) a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
(iii) a covalent bond from X to the α-amino group of the N-terminal amino acid residue of the B chain or to the ε-amino group of a Lys residue present in the B chain of the parent insulin;

wherein X is:
(i) —CO—;
(ii) —COCH(COOH)CO—;
(iii) —CON(CH$_2$COOH)CH$_2$CO—;
(iv) —CON(CH$_2$COOH)CH$_2$CON(CH$_2$COOH)CH$_2$CO—;
(v) —CON(CH$_2$CH$_2$COOH)CH$_2$CH$_2$CO—;
(vi) —CON(CH$_2$CH$_2$COOH)CH$_2$CH$_2$CON(CH$_2$CH$_2$COOH)CH$_2$CH$_2$CO—;
(vii) —CONHCH(COOH)(CH$_2$)$_4$NHCO—;
(viii) —CON(CH$_2$CH$_2$COOH)CH$_2$CO—; or
(ix) —CON(CH$_2$COOH)CH$_2$CH$_2$CO—.

that:
(a) when W is an amino acid residue or a chain of amino acid residues, via a bond from the underscored carbonyl carbon forms an amide bond with an amino group in W; or (b) when W is a covalent bond, via a bond from the underscored carbonyl carbon forms an amide bond with the N-terminal α-amino group in the B chain or with the ε-amino group of a Lys residue present in the B chain of the parent insulin;

wherein Y is:
(i) 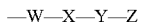a-(CH$_2$)$_m$— where m is an integer in the range of 6 to 32;
(ii) a divalent hydrocarbon chain comprising 1, 2 or 3 —CH═CH— groups and a number of —CH$_2$— groups sufficient to give a total number of carbon atoms in the chain in the range of 10 to 32; or
(iii) a divalent hydrocarbon chain of the formula —(CH$_2$)$_v$C$_6$H(CH$_2$)w- wherein v and w are integers or one of them is zero so that the sum of v and w is in the range of 6 to 30;

wherein Z is:
(i) —COOH;
(ii) —CO-Asp;
(iii) —CO-Glu;
(iv) —CO-Gly;
(v) —CO-Sar;
(vi) —CH(COOH)$_2$;
(vii) —N(CH$_2$COOH)$_2$;
(viii) —SO$_3$H; or
(ix) —PO$_3$H;

and any Zn$^{2+}$ complexes thereof, provided that when W is a covalent bond and X is —CO—, then Z is different from —COOH.

In an alternative or additional embodiment, the side chain —W—X—Y—Z is attached to the α-amino group of the N-terminal amino acid residue of the B chain of the parent insulin.

In an alternative or additional embodiment, the side chain —W—X—Y—Z is attached to the ε-amino group of a Lys residue present in the B chain of the parent insulin.

In an alternative or additional embodiment, the side chain —W—X—Y—Z is attached to the ε-amino group of a Lys residue present in position 28 of the B chain.

In an alternative or additional embodiment, the side chain —W—X—Y—Z is attached to the ε-amino group of a Lys residue present in position 29 of the B chain.

In an alternative or additional embodiment, the side chain —W—X—Y—Z is attached to the ε-amino group of a Lys residue present in position 30 of the B chain.

The substructure W of the side chain —W—X—Y—Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, β-Asp, α-Glu, and γ-Glu. Further options for W are for example α-hGlu and δ-hGlu.

In an alternative or additional embodiment, W is a chain composed of two α-amino acid residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In an alternative or additional embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In an alternative or additional embodiment, W is a chain composed of three α-amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one embodiment, the amino acid residues are codable residues.

In an alternative or additional embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In an alternative or additional embodiment, W can be connected to the ε-amino group of the Lys residue in the B-chain via an urea derivative.

The substructure X of the side chain —W—X—Y—Z can be a group of the formula —$\underline{CO}$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —COCH(COOH)$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment of the first, second, third or fourth aspects of the invention the long-acting insulin, the substructure X of the side chain can be a group of the formula —CON(CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$COOH)CH$_2$CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$CH$_2$COOH)CH$_2$CH$_2$CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin. The substructure Y of the side chain —W—X—Y—Z can be a group of the formula —(CH$_2$)$_m$— where m is an integer in the range of from 6 to 32, from 8 to 20, from 12 to 20, or from 12-16.

In an alternative or additional embodiment, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In an alternative or additional embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In an alternative or additional embodiment, the substructure Z of the side chain —W—X—Y—Z is —COOH provided that when W is a covalent bond and X is —CO—, then Z is different from —COOH. In one embodiment Z is —COOH. In another embodiment, Z is —CO-Asp. In another embodiment, Z is —CO-Glu. In another embodiment, Z is —CO-Gly. In another embodiment, Z is —CO-Sar. In another embodiment, Z is —CH(COOH)$_2$. In another embodiment, Z is —N(CH$_2$COOH)$_2$. In another embodiment, Z is —SO$_3$H. In another embodiment, Z is —PO$_3$H.

In an alternative or additional embodiment, W is selected from the group consisting of α-Asp, β-Asp, α-Glu, and γ-Glu; X is —CO— or —COCH(COOH)CO; Y is —(CH$_2$)$_m$— where m is an integer in the range of 12-18 and Z is —COOH or —CH(COOH)$_2$.

In an alternative, the long-acting or ultra-long-acting insulin, preferably the ultra-long acting insulin, wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin wherein the α-amino acid residue is selected from the group consisting of α-Asp, β-Asp, α-Glu, γ-Glu, α-hGlu and δ-hGlu;

X is:
—CO—;

Y is:
—(CH2)m- where m is an integer in the range of 6 to 32;

Z is:
—COOH;

and any Zn2+ complexes thereof.

The insulin moiety—in the present text also referred to as the parent insulin—of an insulin derivative can be a naturally occurring insulin such as human insulin or porcine insulin. Alternatively, the parent insulin can be an insulin analogue. In one group of parent insulin analogues, the amino acid residue at position A21 is Asn. In another group of parent insulin analogues, the amino acid residue at position A21 is Gly. Specific examples from this group of analogues are $Gly^{A21}$ human insulin, $Gly^{A21}$ des(B30) human insulin; and $Gly^{A21}Arg^{B31}Arg^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is $Asp^{B28}$ human insulin.

In another group of parent insulin analogues, the amino acid residue at position B28 is Lys and the amino acid residue at position B29 is Pro. A specific example from this group of parent insulin analogues is $Lys^{B28}Pro^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is $Thr^{B29}Lys^{B30}$ human insulin.

In another group of parent insulin analogues, the amino acid residue at position B3 is Lys and the amino acid residue at position B29 is Glu. A specific example from this group of parent insulin analogues is $Lys^{B3}Glu^{B29}$ human insulin.

In one embodiment the parent insulin is selected from the group consisting of human insulin; des(B1) human insulin; des(B30) human insulin; GlyA21 human insulin; GlyA21 des(B30) human insulin; AspB28 human insulin; porcine insulin; LysB28ProB29 human insulin; GlyA21ArgB31ArgB32 human insulin; and LysB3GluB29 human insulin.

Examples of '347 derivatives useful in the invention are the following compounds:

$N^{\varepsilon B29}$—($N^{\alpha}$—(HOOC(CH$_2$)$_{14}$CO)-γ-Glu) des(B30) human insulin;
$N^{\varepsilon B29}$—($N^{\alpha}$—(HOOC(CH$_2$)$_{15}$CO)-γ-Glu) des(B30) human insulin;
$N^{\varepsilon B29}$—($N^{\alpha}$—(HOOC(CH$_2$)$_{16}$CO)-γ-Glu) des(B30) human insulin;
$N^{\varepsilon B29}$—($N^{\alpha}$—(HOOC(CH$_2$)$_{17}$CO)-γ-Glu) des(B30) human insulin;
$N^{\varepsilon B29}$—($N^{\alpha}$—(HOOC(CH$_2$)$_{18}$CO)-γ-Glu) des(B30) human insulin;
$N^{\varepsilon B29}$—($N^{\alpha}$—(HOOC(CH$_2$)$_{16}$CO)-γ-Glu-N-(γ-Glu)) des(B30) human insulin;
$N^{\varepsilon B29}$—($N^{\alpha}$-(Asp-OC(CH$_2$)$_{16}$CO)-γ-Glu) des(B30) human insulin;
$N^{\varepsilon B29}$—($N^{\alpha}$-(Glu-OC(CH$_2$)$_{14}$CO)-γ-Glu) des(B30) human insulin;
$N^{\varepsilon B29}$—($N^{\alpha}$-(Glu-OC(CH$_2$)$_{14}$CO—) des(B30) human insulin;
$N^{\varepsilon B29}$—($N^{\alpha}$-(Asp-OC(CH$_2$)$_{16}$CO—) des(B30) human insulin;
$N^{\varepsilon B29}$—($N^{\alpha}$—(HOOC(CH$_2$)$_{16}$CO)-α-Glu-N-(β-Asp)) des(B30) human insulin;
$N^{\varepsilon B29}$—($N^{\alpha}$-(Gly-OC(CH$_2$)$_{13}$CO)-γ-Glu) des(B30) human insulin;
$N^{\varepsilon B29}$—($N^{\alpha}$-(Sar-OC(CH$_2$)$_{13}$CO)-γ-Glu) des(B30) human insulin;
$N^{\varepsilon B29}$—($N^{\alpha}$—(HOOC(CH$_2$)$_{13}$CO)-γ-Glu) des(B30) human insulin;
($N^{\varepsilon B29}$—($N^{\alpha}$—(HOOC(CH$_2$)$_{13}$CO)-β-Asp) des(B30) human insulin;
$N^{\varepsilon B29}$—($N^{\alpha}$—(HOOC(CH$_2$)$_{13}$CO)-α-Glu) des(B30) human insulin;
$N^{\varepsilon B29}$—($N^{\alpha}$—(HOOC(CH$_2$)$_{16}$CO)-γ-D-Glu) des(B30) human insulin;
$N^{\varepsilon B29}$—($N^{\alpha}$—(HOOC(CH$_2$)$_{14}$CO)-γ-D-Asp) des(B30) human insulin;
$N^{\varepsilon B29}$—(N—HOOC(CH$_2$)$_{16}$CO-β-D-Asp) des(B30) human insulin;
$N^{\varepsilon B29}$—(N—HOOC(CH$_2$)$_{14}$CO-IDA) des(B30) human insulin;
$N^{\varepsilon B29}$—[N—(HOOC(CH$_2$)$_{16}$CO)—N-(carboxyethyl)-Gly] des(B30) human insulin;
$N^{\varepsilon B29}$—[N—(HOOC(CH$_2$)$_{14}$CO)—N-(carboxyethyl)-Gly] des(B30) human insulin; and
$N^{\varepsilon B29}$—[N—(HOOC(CH$_2$)$_{14}$CO)—N-(carboxymethyl)-β-Ala]des(B30) human insulin.

In an alternative or additional embodiment of the first, second, third or fourth aspects of the invention the insulin is $N^{\varepsilon B29}$—($N^{\alpha}$—(HOOC(CH$_2$)$_{14}$CO)-γ-Glu) des(B30) human insulin. In an alternative or additional embodiment of the first, second, third or fourth aspects of the invention the insulin is $N^{B29}$—($N^{\alpha}$—(HOOC(CH$_2$)$_{15}$CO)-γ-Glu) des(B30) human insulin. In an alternative or additional embodiment of the first, second, third or fourth aspects of the invention the insulin is $N^{\varepsilon B29}$—($N^{\alpha}$—(HOOC(CH$_2$)$_{16}$CO)-γ-Glu) des(B30) human insulin. In one embodiment the insulin is $N^{\varepsilon B29}$—($N^{\alpha}$—(HOOC(CH$_2$)$_{17}$CO)-γ-Glu) des(B30) human insulin. In an alternative or additional embodiment of the first, second, third or fourth aspects of the invention the insulin $N^{\varepsilon B29}$—($N^{\alpha}$—(HOOC(CH$_2$)$_{18}$CO)-γ-Glu) des(B30) human insulin. In an alternative or additional embodiment of the first, second, third or fourth aspects of the invention the insulin is $N^{B29}$—($N^{\alpha}$—(HOOC(CH$_2$)$_{16}$CO)-γ-Glu-N-(γ-Glu)) des(B30) human insulin. In an alternative or additional embodiment of the first, second, third or fourth aspects of the invention the insulin is $N^{\varepsilon B29}$—($N^{\alpha}$-(Asp-OC(CH$_2$)$_{16}$CO)-γ-Glu) des(B30) human insulin. In an alternative or additional embodiment of the first, second, third or fourth aspects of the invention the insulin is $N^{\varepsilon B29}$—($N^{\alpha}$-

(Glu-OC(CH$_2$)$_{14}$CO)-γ-Glu) des(B30) human insulin. In an alternative or additional embodiment of the first, second, third or fourth aspects of the invention the insulin is N$^{εB29}$—(N$^α$-(Glu-OC(CH$_2$)$_{14}$CO—) des(B30) human insulin. In an alternative or additional embodiment of the first, second, third or fourth aspects of the invention the insulin is N$^{εB29}$—(N$^α$-(Asp-OC(CH$_2$)$_{16}$CO—) des(B30) human insulin. In an alternative or additional embodiment of the first, second, third or fourth aspects of the invention the insulin is N$^{εB29}$—(N$^α$—(HOOC(CH$_2$)$_{16}$CO)-α-Glu-N-(β-Asp)) des(B30) human insulin. In an alternative or additional embodiment of the first, second, third or fourth aspects of the invention the insulin is N$^{εB29}$—(N$^α$-(Gly-OC(CH$_2$)$_{13}$CO)-γ-Glu) des(B30) human insulin. In an alternative or additional embodiment of the first, second, third or fourth aspects of the invention the insulin is N$^{εB29}$—(N$^α$-(Sar-OC(CH$_2$)$_{13}$CO)-γ-Glu) des(B30) human insulin. In an alternative or additional embodiment of the first, second, third or fourth aspects of the invention the insulin is N$^{εB29}$—(N$^α$—(HOOC(CH$_2$)$_{13}$CO)-γ-Glu) des(B30) human insulin. In an alternative or additional embodiment of the first, second, third or fourth aspects of the invention the insulin is (N$^{εB29}$—(N$^α$—(HOOC(CH$_2$)$_{13}$CO)-β-Asp) des(B30) human insulin. In an alternative or additional embodiment of the first, second, third or fourth aspects of the invention the insulin is N$^{εB29}$—(N$^α$—(HOOC(CH$_2$)$_{13}$CO)-α-Glu) des(B30) human insulin. In an alternative or additional embodiment of the first, second, third or fourth aspects of the invention the insulin is N$^{εB29}$—(N$^α$—(HOOC(CH$_2$)$_{16}$CO)-γ-D-Glu) des(B30) human insulin. In an alternative or additional embodiment of the first, second, third or fourth aspects of the invention the insulin is N$^{εB29}$—(N$^α$—(HOOC(CH$_2$)$_{14}$CO)-β-D-Asp) des(B30) human insulin. In an alternative or additional embodiment of the first, second, third or fourth aspects of the invention the insulin is N$^{εB29}$—(N$^α$—(HOOC(CH$_2$)$_{14}$CO)-β-D-Asp) des(B30) human insulin. In an alternative or additional embodiment of the first, second, third or fourth aspects of the invention the insulin is N$^{εB29}$—(N—HOOC(CH$_2$)$_{16}$CO-β-D-Asp) des(B30) human insulin. In an alternative or additional embodiment of the first, second, third or fourth aspects of the invention the insulin is N$^{εB29}$—(N—HOOC(CH$_2$)$_{14}$CO-IDA) des(B30) human insulin. In an alternative or additional embodiment of the first, second, third or fourth aspects of the invention the insulin is N$^{εB29}$—[N—(HOOC(CH$_2$)$_{16}$CO)—N-(carboxyethyl)-Gly]des(B30) human insulin. In an alternative or additional embodiment of the first, second, third or fourth aspects of the invention the insulin is N$^{εB29}$—[N—(HOOC(CH$_2$)$_{14}$CO)—N-(carboxyethyl)-Gly]des(B30) human insulin. In an alternative or additional embodiment of the first, second, third or fourth aspects of the invention the insulin is N$^{εB29}$—[N—(HOOC(CH$_2$)$_{14}$CO)—N-(carboxymethyl)-β-Ala]des(B30) human insulin.

In an alternative or additional embodiment of the first, second, third or fourth aspects of the invention the insulin is provided in the form of essentially zinc free compounds or in the form of zinc complexes. When zinc complexes of a hexameric insulin or insulin derivative are provided, two Zn$^{2+}$ ions, three Zn$^{2+}$ ions or four Zn$^{2+}$ ions may be bound to each insulin hexamer. In an alternative or additional embodiment of the first, second, third or fourth aspects of the invention the insulin is a hexameric insulin or insulin derivative in the form of a zinc complex, wherein each insulin hexamer binds two zinc ions, three zinc ions, four zinc ions, five zinc ions, six zinc ions, seven zinc ions, eight zinc ions, nine zinc ions or ten zinc ions. Solutions of zinc complexes of the insulin derivatives will contain mixtures of such species.

Details pertaining to the preparation, formulation, pharmacology and other characteristics of relevance for the '347 derivatives are set forth in WO 2005/012347, which is hereby incorporated by reference herein.

In an alternative or additional embodiment of the first, second, third or fourth aspects of the invention the ultra-long-acting insulin is LysB29(Nε-hexadecandioyl-γ-Glu) des(B30) human insulin (insulin degludec, Tresiba®).

In an alternative or additional embodiment of the first, second, third or fourth aspects of the invention the long-acting insulin is selected from the group consisting of:

(a) neutral protamine hagedorn insulin (NHP insulin) (Humulin® N, Novolin® ge NPH);
(b) Lente Insulin (Humulin® L, Novolin® ge Lente);
(c) Ultralente Insulin (Humulin® U, Novolin™ ge Ultralente);
(d) Glargine Insulin (Lantus®);
(e) Detemir Insulin (Levemir®);
(f) Hypurin Bovine Lente; and
(g) Hypurin Bovine PZI.

For some embodiments, the long-acting or ultra-long-acting insulin compound has an overall hydrophobicity which is essentially similar to that of human insulin.

For some embodiments, the long-acting or ultra-long-acting insulin compound has a hydrophobic index, k'$_{rel}$, which is in the range from about 0.02 to about 10, from about 0.1 to about 5; from about 0.5 to about 5; or from about 0.5 to about 2.

For some embodiments, the long-acting or ultra-long-acting insulin compound is soluble at physiological pH values, such as pH values in the interval from about 6.5 to about 8.5.

For some embodiments, the second insulin-like compound is soluble at physiological pH values, such as pH values in the interval from about 6.5 to about 8.5.

When an insulin-like compound according to the invention is stated to be "soluble at physiological pH values" it means that the insulin derivative can be used for preparing injectable insulin compositions that are fully dissolved at physiological pH values. Such favourable solubility may either be due to the inherent properties of the insulin-like compound alone or a result of a favourable interaction between the insulin derivative and one or more ingredients contained in the vehicle.

For some embodiments of the present invention, the combination of the present invention is used to treat a subject that is at least 20 years.

For some embodiments of the present invention, the combination of the present invention is used to treat a subject whose body mass index is no greater than 35 kg/m$^2$.

For some embodiments of the present invention, the combination of the present invention is used to treat a subject whose body mass index is about 25 kg/m$^2$.

For some embodiments of the present invention, the combination of the present invention is used to treat a subject whose baseline HbA$_{1c}$ level before treatment is greater than 7%, such as about 8% or 9%.

For some embodiments of the present invention, the combination of the present invention is used to treat a subject that has been suffering from diabetes for at least 1 year, such as at least 5 years, such as at least 10 years.

For some embodiments of the present invention, the combination of the present invention is capable of achieving a baseline $HbA_{1c}$ level for the subject being no more than 7 after 26 weeks of treatment.

For some embodiments of the present invention, the long-acting or ultra-long-acting insulin for use according to the present invention is delivered by injection, such as by use of an insulin pen device.

For some embodiments of the present invention, the long-acting or ultra-long-acting insulin for use according to the present invention is delivered by injection together with and in the same formulation as a second insulin-like compound or GLP-1 compound, such as by use of an insulin pen device.

For some embodiments of the present invention, said insulin pen device is FlexPen®(s) or FlexTouch®(s). FlexPen® and or FlexTouch® are trademarks of Novo Nordisk A/S.

In an alternative or additional embodiment of the first, second, third or fourth aspects of the invention the long-acting or ultra-long-acting insulin is administered, either concurrently or consecutively, together with a one or more additional drug used in the treatment of diabetes.

In an alternative or additional embodiment of the first, second, third or fourth aspects of the invention, the one or more additional drug used in the treatment of diabetes is, or includes, a drug selected from the group consisting of: insulins, sensitizers (such as biguanides and thiazolidinediones), secretagogues (such as sulfonylureas and nonsulfonylurea secretagogues), alpha-glucosidase inhibitors and peptide analogs (such as injectable incretin mimetics, gastric inhibitory peptide analogs, dipeptidyl peptidase-4 inhibitors and injectable amylin analogues).

In an alternative or additional embodiment of the first, second, third or fourth aspects of the invention, the one or more additional drug used in the treatment of diabetes is, or includes, a biguanide selected from the group consisting of: metformin, phenformin, buformin and proguanil.

In an alternative or additional embodiment of the first, second, third or fourth aspects of the invention, the one or more additional drug used in the treatment of diabetes is, or includes, a thiazolidinedione selected from the group consisting of: rosiglitazone (Avandia®), and pioglitazone (Actos®).

In an alternative or additional embodiment of the first, second, third or fourth aspects of the invention, the one or more additional drug used in the treatment of diabetes is, or includes, a sulfonylurea selected from the group consisting of: carbutamide, acetohexamide, chlorpropamide, tolbutamide, tolazamide, glipizide, gliclazide, glibenclamide (glyburide), glibornuride, gliquidone, glisoxepide, glyclopyramide and glimepiride.

In an alternative or additional embodiment of the first, second, third or fourth aspects of the invention, the one or more additional drug used in the treatment of diabetes is, or includes, a nonsulfonylurea secretagogue selected from the group consisting of: repaglinide (Prandin®) and nateglinide (Starlix®).

In an alternative or additional embodiment of the first, second, third or fourth aspects of the invention, the one or more additional drug used in the treatment of diabetes is, or includes, an alpha-glucosidase inhibitor selected from the group consisting of: acarbose (Precose®), miglitol (Glyset®) and voglibose.

In an alternative or additional embodiment of the first, second, third or fourth aspects of the invention, the one or more additional drug used in the treatment of diabetes is, or includes, an injectable incretin mimetic selected from the group consisting of: exenatide (exendin-4, Byetta®, Bydureon®), liraglutide (Victoza®), albiglutide, dulaglutide and lixisenatide (Lyxumia®).

In an alternative or additional embodiment of the first, second, third or fourth aspects of the invention, the one or more additional drug used in the treatment of diabetes is, or includes, a dipeptidyl peptidase-4 inhibitor selected from the group consisting of: sitagliptin (Januvia®), vildagliptin (Galvus®), saxagliptin (Onglyza®), linagliptin (Trajenta®), dutogliptin, gemigliptin, alogliptin and berberine.

In an alternative or additional embodiment of the first, second, third or fourth aspects of the invention, the one or more additional drug used in the treatment of diabetes is, or includes, an injectable amylin analogue selected from the group consisting of: pramlintide.

In an alternative or additional embodiment of the first, second, third or fourth aspects of the invention, the one or more additional drug used in the treatment of diabetes is, or includes, rapid-acting insulins.

In an alternative or additional embodiment of the first, second, third or fourth aspects of the invention, the one or more additional drug used in the treatment of diabetes is, or includes, a rapid-acting insulin selected from the group consisting of insulin aspart, insulin glulisine and insulin lispro.

In an alternative or additional embodiment of the first, second, third or fourth aspects of the invention, the long-acting or ultra-long-acting insulin is formulated together with a pharmaceutically acceptable carrier, vehicle, diluent and or excipient. The carrier(s) must be "acceptable" in the sense of being compatible with the compound of the invention and not deleterious to the recipients thereof. Typically, the carriers will be water or saline which will be sterile and pyrogen-free.

The long-acting or ultra-long-acting insulin compound for use according to the present invention and a second insulin-like compound can if necessary be mixed in a ratio from about 90/10%; about 85/15%, about 80/20%, about 70/30%, about 60/40%, about 50/50%, about 40/60%, about 30/60% or about 10/90%. In one embodiment, said second insulin-like compound is a rapid-acting insulin.

In another embodiment, the long-acting or ultra-long-acting insulin compound for use according to the present invention and the second insulin-like compound according to the present invention can if necessary be mixed in a ratio from 40% or more of the basal to 60% or less of the second insulin-like compound, from more than 50% or more of the basal to less than 50% of the second insulin-like compound, or from about 70% or more of the basal to about 30% or less of the second insulin-like compound. In one embodiment, said second insulin-like compound is a rapid-acting insulin.

In another embodiment, the long-acting or ultra-long-acting insulin compound for use according to the present invention is present in a pharmaceutical composition which is a solution containing from about 120 nmol/mL to about 2400 nmol/mL, from about 400 nmol/mL to about 2400 nmol/mL, from about 400 nmol/mL to about 1200 nmol/mL, from about 600 nmol/mL to about 2400 nmol/mL, or from about 600 nmol/mL to about 1200 nmol/mL of said long-acting insulin, or of said long-acting insulin and second insulin-like compound.

In the combination of the present invention, the long-acting or ultra-long-acting insulin or each of the long-acting or ultra-long-acting insulin and second insulin-like compound may be in an amount of from about 0.01 to about 5 U/kg, typically from about 0.03 to about 3 U/kg.

In one embodiment of the present invention the concentration of the long-acting or ultra-long-acting insulin for use according to the present invention in the pharmaceutical composition is 100 U/mL.

In one embodiment of the present invention the concentration of the long-acting or ultra-long-acting insulin for use according to the present invention in the pharmaceutical composition is 200 U/mL.

A pharmaceutical composition containing a naturally occurring insulin, an insulin analogue, or a derivative of a naturally occurring insulin or insulin analogue is termed "an insulin composition" herein. In order to exercise the present invention an insulin composition may be administered parenterally to patients in need of such a treatment. Parenteral administration may be performed by injection, such as subcutaneous, intramuscular or intravenous injection, by means of a syringe, optionally a pen-like syringe. In one embodiment the administration is by subcutaneous, injection. In one embodiment the administration is by intramuscular injection. In one embodiment the administration is by intravenous injection. Alternatively, parenteral administration can be performed by means of an infusion pump.

Injectable insulin compositions can be prepared using the conventional techniques of the pharmaceutical industry which involve dissolving and mixing the ingredients as appropriate to give the desired end product. Thus, according to one procedure, a natural insulin, analogue or derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer is typically selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative useful in embodiments of the invention.

In a further embodiment of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/mL to 20 mg/mL. In a further embodiment of the invention the preservative is present in a concentration from 0.1 mg/mL to 5 mg/mL. In a further embodiment of the invention the preservative is present in a concentration from 5 mg/mL to 10 mg/mL. In a further embodiment of the invention the preservative is present in a concentration from 10 mg/mL to 20 mg/mL. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19th edition, 1995.

In a further embodiment of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/mL and about 150 mg/mL. In a further embodiment of the invention the isotonic agent is present in a concentration from 1 mg/mL to 50 mg/mL. In a further embodiment of the invention the isotonic agent is present in a concentration from 1 mg/mL to 7 mg/mL. In a further embodiment of the invention the isotonic agent is present in a concentration from 8 mg/mL to 24 mg/mL. In a further embodiment of the invention the isotonic agent is present in a concentration from 25 mg/mL to 50 mg/mL. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19th edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid), TRIS (2ε-amino-2-hydroxymethyl-1,3-propandiol), and sodium phosphate.

Insulin compositions can be used in the treatment of states which are sensitive to insulin. Thus, they can be used in the treatment of type 1 diabetes mellitus, type 2 diabetes mellitus and hyperglycaemia for example as sometimes seen in seriously injured persons and persons who have undergone major surgery. The optimal dose level for any patient will depend on a variety of factors including the efficacy of the specific insulin, analogue or derivative employed, the age, body weight, physical activity, and diet of the patient, on a possible combination with other drugs, and on the severity of the state to be treated. It is recommended that the dosage regimen be determined for each individual patient by those skilled in the art in a similar way as for known insulin compositions, however taking into consideration the present teachings concerning dosage intervals.

Where expedient, the insulin compositions may be used in combination with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

In one embodiment the composition of the invention is as defined in WO 2007/074133 or WO2008/152106.

The long-acting or ultra-long-acting insulin and the one or more additional drug used in the treatment of diabetes may be administered concurrently in the same formulation.

In an alternative or additional embodiment of the first, second, third or fourth aspects of the invention, the one or more additional drug used in the treatment of diabetes is, or includes, liraglutide.

In an alternative or additional embodiment of the first, second, third or fourth aspects of the invention, the insulin is LysB29(Nε-hexadecandioyl-γ-Glu) des(B30) human insulin (insulin degludec, Tresiba®) and the insulin is administered, concurrently or consecutively, with liraglutide.

In an alternative or additional embodiment of the first, second, third or fourth aspects of the invention, the a disease or condition where administration of insulin will be of benefit is selected from the group consisting of diabetes mellitus, such as type 1 diabetes mellitus or type 2 diabetes mellitus, other conditions characterised by hyperglycaemia (such as pre-diabetes, impaired glucose tolerance, metabolic syndrome, obesity, cachexia, in vivo beta-cell loss/death, excessive appetite and inflammation.

The term "diabetes" or "diabetes mellitus" includes type 1 diabetes mellitus, type 2 diabetes mellitus, gestational diabetes (during pregnancy) and other states that cause hyperglycemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes mellitus, also called insulin-dependent diabetes mellitus (IDDM) and juvenile-onset diabetes, is caused by B-cell destruction, usually leading to absolute insulin deficiency.

Type 2 diabetes mellitus, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Hence, in an alternative or additional embodiment of the first, second, third or fourth aspects of the invention, the disease or condition where administration of insulin will be of benefit is diabetes mellitus. The diabetes mellitus may be type 1 diabetes mellitus. The diabetes mellitus may be type 2 diabetes mellitus.

In an alternative or additional embodiment of the first, second, third or fourth aspects of the invention no long-acting insulin, or substantially no long-acting insulin, is administered to the individual in need of treatment other than that administered in step (c).

In an alternative or additional embodiment of the first, second, third or fourth aspects of the invention no insulin, or substantially no, insulin is administered to the individual in need of treatment other than that administered in step (c). By 'insulin' we include any natural insulin or derivative thereof.

In one embodiment, the first aspect of the present invention provides insulin degludec (Tresiba®) for use in treating type 2 or type 1 diabetes mellitus, wherein the administration of the insulin degludec comprises or consists of the following steps:

(a) optionally providing a (optionally capillary) blood or plasma sample to be tested from an individual in need of treatment;
(b) taking a single fasting self-measured blood or plasma glucose measurement from said individual in need of treatment;
(c) using the single fasting blood or plasma glucose measurement to determine the insulin degludec dose to be administered; and
(d) administering the insulin degludec to the individual at the dose determined in step (c),
wherein steps (a) to (c) are performed on the same day, wherein, in step (d), the insulin degludec is administered at a frequency of about once per day for an administration period of 7 days starting on the same day as steps (a) to (c), and wherein said steps (a) to (d) are repeated continuously as long as needed by the said individual.

In one embodiment, the invention provides a long acting or ultra-long-acting insulin as defined herein, such as insulin degludec, for use in treating type 1 or type 2 diabetes mellitus, wherein the administration of said insulin comprises or consists of the following steps:

(a) optionally providing a (optionally capillary) blood or plasma sample from an individual in need of treatment with said insulin, on a given day;
(b) taking a single fasting self-measured blood or plasma glucose measurement from the sample provided in step (a), on the same day as step (a);
(c) using the single fasting blood or plasma glucose measurement of step (b) to determine, on the same day as steps (a) and (b), the dose of said insulin to be administered to said individual;
(d) administering said insulin to said individual at the dose determined in step (c), starting on the same day as steps (a) to (c) and for an administration period of 7 days or of between 6 and 8 days or of between 5 and 9 days; and
(e) on the day following the last day of the period of administration of step (d), repeating steps (a) to (c) on the same day, then (d) again starting on the same day as (a) to (c) and for another administration period of 7 days or of between 6 and 8 days or of between 5 and 9 days, wherein steps (a) to (d) can so be repeated as long as needed by said individual.

Accordingly, the second aspect of the invention provides a method of treating type 2 or type 1 diabetes mellitus, comprising or consisting of the following steps:

(a) providing a capillary blood or plasma sample to be tested from an individual in need of treatment;
(b) taking a single fasting self-measured blood or plasma glucose measurement from an individual in need of treatment;
(c) using the single fasting blood or plasma glucose measurement to determine an insulin degludec dose to be administered; and
(d) administering the insulin degludec to the individual at the dose determined in step (c),
wherein steps (a) to (c) are performed on the same day, wherein, in step (d), the insulin degludec is administered at a frequency of about once per day for an administration period of 7 days starting on the same day as steps (a) to (c), and wherein said steps (a) to (d) are repeated continuously as long as needed by the said individual.

Accordingly, the third aspect of the invention provides a method of determining an insulin degludec dose to be administered to an individual suffering from type 2 diabetes mellitus comprising or consisting of the following steps:

(a) providing a capillary blood or plasma sample to be tested from an individual in need of treatment;
(b) taking a single fasting self-measured blood or plasma glucose measurement from an individual in need of treatment; and
(c) using the single fasting blood or plasma glucose measurement to determine an insulin degludec dose to be administered, wherein steps (a) to (c) are performed on the same day and are repeated every 7 days, or every 5, 6, 7, 8 or 9 days, as long as needed by the said individual.

Further Embodiments

1. A long-acting or ultra-long-acting insulin for use in treating a disease or condition where administration of insulin will be of benefit, wherein the administration of said insulin comprises or consists of the following steps:
   (a) optionally providing a blood sample to be tested from an individual in need of treatment;
   (b) taking a single fasting blood or plasma glucose measurement from said individual in need of treatment;
   (c) using the single fasting blood or plasma glucose measurement to determine the insulin dose to be administered; and
   (d) administering said insulin to the individual at the dose determined in step (c).
2. The long-acting or ultra-long-acting insulin for use according to embodiment 1 wherein, in step (d), said insulin is administered once, or at least once, every 72 hours, for example, said insulin may be administered once, or at least once, every 64 hours; once, or at least once, every 56 hours; once, or at least once, every 48 hours; once, or at least once, every 42 hours; once, or at least once, every 40 hours; once, or at least once, every 36 hours; once, or at least once, every 32 hours; once, or at least once, every 30 hours; once, or at least once, every 24 hours; once, or at least once, every 18 hours; once, or at least once, every 16 hours; or said insulin is administered once, or at least once, every 8 hours.
3. The long-acting or ultra-long-acting insulin for use according to embodiment 1 or 2, wherein, in step (d), said insulin is administered once, or at least once, every 8 to 72 hours, for example, once, or at least once, every 64 to 8 hours; once, or at least once, every 56 to 8 hours; once, or at least once, every 48 to 8 hours; once, or at least once, every 40 to 8 hours; once, or at least once, every 36 to 8 hours; once, or at least once, every 32 to 16 hours; once, or at least once, every 28 to 20 hours; once, or at least once, every 26 to 22 hours; once, or at least once, every 24 to 8 hours; once, or at least once, every 20 to 8 hours; or said insulin is administered once, or at least once, every 16 to 8 hours.
4. The long-acting or ultra-long-acting insulin for use according to any one of embodiments 1 to 3, wherein, in step (d), said insulin is administered once, or at least once, every 40 to 8 hours.
5. The long-acting or ultra-long-acting insulin for use according to any one of the preceding embodiments, wherein, in step (d), said insulin is administered once every 40 to 8 hours.
6. The long-acting or ultra-long-acting for use according to any one of the preceding embodiments, wherein, in step (d), said insulin is administered once, or at least once, every 24 hours.
7. The long-acting or ultra-long-acting insulin for use according to any one of the preceding embodiments, wherein, in step (d), said insulin is administered once every 24 hours.
8. The long-acting or ultra-long-acting insulin for use according to any one of the preceding embodiments, wherein step (d) is performed for an administration period of, or at least of, 1 day; for example, of, or at least of, 2 days; of, or at least of, 3 days; of, or at least of, 4 days; of, or at least of, 5 days; of, or at least of, 6 days; of, or at least of, 7 days; of, or at least of, 8 days; of, or at least of, 9 days; of, or at least of, 10 days; of, or at least of, 11 days; of, or at least of, 12 days; of, or at least of, 13 days; of, or at least of, 14 days or for an administration period of, or at least of, 15 days.
9. The long-acting or ultra-long-acting insulin for use according to embodiment 8, wherein step (d) is performed for an administration period of between 1 and 15 days, for example, between 1 and 13 days; between 2 and 12 days; between 3 and 11 days; between 4 and 10 days; between 5 and 9 days; or for an administration period of between 6 and 8 days.
10. The long-acting or ultra-long-acting insulin for use according to embodiment 8, wherein step (d) is performed for an administration period of, or at least of, 7 days.
11. The long-acting or ultra-long-acting insulin for use according to embodiment 8 or 9, wherein step (d) is performed for an administration period of 7 days.
12. The long-acting or ultra-long-acting insulin for use according to any one of the preceding embodiments, wherein the said insulin administration comprises or consists of steps (a) to (d) and the following step(s):
    (e) repeating steps (a) to (d).
13. The long-acting or ultra-long-acting insulin for use according to embodiment 12, wherein, in step (e), steps (a) to (d) are repeated continuously and:
    (i) wherein the administration period of each step (d) is of the same duration or same range of duration in each repetition of steps (a) to (d); or
    (ii) wherein the administration period of each step (d) is of the same duration or same range of duration in each repetition of steps (a) to (d) until a target fasting blood glucose level is achieved in the individual in need of treatment, after which, the duration or range of duration of the administration of step (d) in subsequent repetitions of steps (a) to (d) is increased.
14. The long-acting or ultra-long-acting insulin for use according to embodiment 13, wherein, in step (e), steps (a) to (d) are repeated contiguously.
15. The long-acting or ultra-long-acting insulin for use according to embodiments 13 or 14, wherein, in step (e)(ii), once the target blood glucose level is achieved in the individual in need of treatment, step (d) is then performed for an administration period of, or at least of, 2 weeks; for example, for an administration period of, or at least of, 3 weeks.
16. a. The long-acting or ultra-long-acting insulin for use according to any one of embodiments 13 to 15, wherein, in step (e)(ii) steps (a) to (d) are repeated continuously until the target blood glucose level is achieved in 1, or at least 1, step (b), for example, 2, or at least 2, consecutive repetitions of step (b); 3, or at least 3, consecutive repetitions of step (b); 4, or at least 4, consecutive repetitions of step (b); 5, or at least 5, consecutive repetitions of step (b); 6, or at least 6, consecutive repetitions of step (b); 7, or at least 7, consecutive repetitions of step (b); 8, or at least 8, consecutive repetitions of step (b); 9, or at least 9, consecutive repetitions of step (b); 10, or at least 10, consecutive repetitions of step (b).

16.b. The long-acting or ultra-long-acting insulin for use according to any one of embodiments 1 to 16.a.,
wherein, steps (a) to (c) are performed on the same day,
wherein, in step (d), the said insulin is administered for an administration period of between 1 and 15 days and starting on the same day as steps (a) to (c) (after step (c)), for example, for an administration period of between 1 and 13 days; between 2 and 12 days; between 3 and 11 days; between 4 and 10 days; between 5 and 9 days; or of between 6 and 8 days, or of 7 days, and
wherein said steps (a) to (d) are repeated continuously as long as needed by the said individual.

16.c. The long-acting or ultra-long-acting insulin for use according to any one of embodiments 1 to 16.b.,
wherein, steps (a) to (c) are performed on the same day,
wherein, in step (d), the said insulin is administered at a frequency of about once per day for an administration period of 7 days starting on the same day as steps (a) to (c), and
wherein said steps (a) to (d) are repeated continuously as long as needed by the said individual.

16.c. The long-acting or ultra-long-acting insulin for use according to embodiment 16.b. wherein said insulin is insulin degludec.

17. The long-acting or ultra-long-acting insulin for use according to any one of the preceding embodiments wherein, in step (c), the insulin dose to be administered is determined using titration.

18. The long-acting or ultra-long-acting insulin for use according to any one of the preceding embodiments wherein, in step (b), the single fasting blood or plasma glucose measurement is performed using a self-measurement blood glucose (SMBG) test.

19. The long-acting or ultra-long-acting insulin for use according to any one of the preceding embodiments wherein, in step (b), the single fasting blood or plasma glucose measurement is performed using a self-measurement plasma glucose (SMPG) test.

20. The long-acting or ultra-long-acting insulin for use according to any one of embodiments 1 to 4 wherein, prior to step (b), the initial insulin is administered in a first administration period at a dose of 10 U.

21. The long-acting or ultra-long-acting insulin for use according to any one of embodiments 1 to 5 wherein, in step (b) the single blood or plasma glucose measurement taken from the individual in need of treatment in step (c) is a plasma glucose measurement of:
≤3.9 mmol/L (≤70 mg/dL): the dose administered in step (d) is reduced by 4 U compared to the dose previously administered;
4 to 5 mmol/L (71 to 90 mg/dL): the dose administered in step (d) is unaltered compared to the dose previously administered; or
≥5.1 mmol/L (≥91 mg/dL): the dose administered in step (d) is increased by 4 U compared to the dose previously administered.

22. a. The long-acting or ultra-long-acting insulin for use according to any one of the preceding embodiments wherein said insulin is an ultra-long acting insulin.

22.b. The long-acting or ultra-long-acting insulin for use according to any one of embodiments 1 to 21 wherein said insulin is a long-acting insulin.

23. a. The long-acting or ultra-long-acting insulin for use according to any one of the preceding embodiments wherein said insulin has a side chain attached to the α-amino group of the N-terminal amino acid residue of the B chain or to the ε-amino group of the Lys residue present in the B chain of the parent insulin, the side chain being of the general formula:

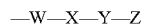

—W—X—Y—Z wherein W is:
(iv) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
(v) a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
(vi) a covalent bond from X to the α-amino group of the N-terminal amino acid residue of the B chain or to the ε-amino group of a Lys residue present in the B chain of the parent insulin;

wherein X is:
(x) —CO—;
(xi) —COCH(COOH)CO—;
(xii) —CON(CH$_2$COOH)CH$_2$CO—;
(xiii) —CON(CH$_2$COOH)CH$_2$CON(CH$_2$COOH) CH$_2$CO—;
(xiv) —CON(CH$_2$CH$_2$COOH)CH$_2$CH$_2$CO—;
(xv) —CON(CH$_2$CH$_2$COOH)CH$_2$CH$_2$CON (CH$_2$CH$_2$COOH)CH$_2$CH$_2$CO—;
(xvi) —CONHCH(COOH)(CH$_2$)$_4$NHCO—;
(xvii) —CON(CH$_2$CH$_2$COOH)CH$_2$CO—; or
(xviii) —CON(CH$_2$COOH)CH$_2$CH$_2$CO—.

that:
(c) when W is an amino acid residue or a chain of amino acid residues, via a bond from the underscored carbonyl carbon forms an amide bond with an amino group in W; or
(d) when W is a covalent bond, via a bond from the underscored carbonyl carbon forms an amide bond with the N-terminal α-amino group in the B chain or with the ε-amino group of a Lys residue present in the B chain of the parent insulin;

wherein Y is:
(iv) a-(CH$_2$)$_m$— where m is an integer in the range of 6 to 32;
(v) a divalent hydrocarbon chain comprising 1, 2 or 3 —CH═CH— groups and a number of —CH$_2$— groups sufficient to give a total number of carbon atoms in the chain in the range of 10 to 32; or
(vi) a divalent hydrocarbon chain of the formula —(CH$_2$)$_v$C$_6$H(CH$_2$)w- wherein v and w are integers or one of them is zero so that the sum of v and w is in the range of 6 to 30;

wherein Z is:
(x) —COOH;
(xi) —CO-Asp;
(xii) —CO-Glu;

(xiii) —CO-Gly;
(xiv) —CO-Sar;
(xv) —CH(COOH)$_2$;
(xvi) —N(CH$_2$COOH)$_2$;
(xvii) —SO$_3$H; or
(xviii) —PO$_3$H;
and any Zn$^{2+}$ complexes thereof, provided that when W is a covalent bond and X is —CO—, then Z is different from —COOH.

23.b. The long-acting or ultra-long-acting insulin, preferably the ultra-long acting insulin, according to paragraph 23.a. wherein said derivative has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin wherein the α-amino acid residue is selected from the group consisting of α-Asp, β-Asp, α-Glu, γ-Glu, α-hGlu and δ-hGlu;

X is:
—CO—;
Y is:
—(CH2)m- where m is an integer in the range of 6 to 32;
Z is:
—COOH;
and any Zn2+ complexes thereof.

24. a. The long-acting or ultra-long-acting insulin for use according to embodiment 22 a. or b. or 23 a. or b. wherein said insulin is selected from:
N$^{εB29}$—(N$^α$—(HOOC(CH$_2$)$_{14}$CO)-γ-Glu) des(B30) human insulin;
N$^{εB29}$—(N$^α$—(HOOC(CH$_2$)$_{15}$CO)-γ-Glu) des(B30) human insulin;
N$^{εB29}$—(N$^α$—(HOOC(CH$_2$)$_{16}$CO)-γ-Glu) des(B30) human insulin;
N$^{εB29}$—(N$^α$—(HOOC(CH$_2$)$_{17}$CO)-γ-Glu) des(B30) human insulin;
N$^{εB29}$—(N$^α$—(HOOC(CH$_2$)$_{18}$CO)-γ-Glu) des(B30) human insulin;
N$^{εB29}$—(N$^α$—(HOOC(CH$_2$)$_{16}$CO)-γ-Glu-N-(γ-Glu)) des(B30) human insulin;
N$^{εB29}$—(N$^α$-(Asp-OC(CH$_2$)$_{16}$CO)-γ-Glu) des(B30) human insulin;
N$^{εB29}$—(N$^α$-(Glu-OC(CH$_2$)$_{14}$CO)-γ-Glu) des(B30) human insulin;
N$^{εB29}$—(N$^α$-(Glu-OC(CH$_2$)$_{14}$CO—) des(B30) human insulin;
N$^{εB29}$—(N$^α$-(Asp-OC(CH$_2$)$_{16}$CO—) des(B30) human insulin;
N$^{εB29}$—(N$^α$—(HOOC(CH$_2$)$_{16}$CO)-α-Glu-N-(β-Asp)) des(B30) human insulin;
N$^{εB29}$—(N$^α$-(Gly-OC(CH$_2$)$_{13}$CO)-γ-Glu) des(B30) human insulin;
N$^{εB29}$—(N$^α$-(Sar-OC(CH$_2$)$_{13}$CO)-γ-Glu) des(B30) human insulin;
N$^{εB29}$—(N$^α$—(HOOC(CH$_2$)$_{13}$CO)-γ-Glu) des(B30) human insulin;
N$^{εB29}$—(N$^α$—(HOOC(CH$_2$)$_{13}$CO)-β-Asp) des(B30) human insulin;
N$^{εB29}$—(N$^α$—(HOOC(CH$_2$)$_{13}$CO)-α-Glu) des(B30) human insulin;
N$^{εB29}$—(N$^α$—(HOOC(CH$_2$)$_{16}$CO)-γ-D-Glu) des(B30) human insulin;
N$^{εB29}$—(N$^α$—(HOOC(CH$_2$)$_{14}$CO)-β-D-Asp) des(B30) human insulin;
N$^{εB29}$—(N—HOOC(CH$_2$)$_{16}$CO-β-D-Asp) des(B30) human insulin;
N$^{εB29}$—(N—HOOC(CH$_2$)$_{14}$CO-IDA) des(B30) human insulin;
N$^{εB29}$—[N—(HOOC(CH$_2$)$_{16}$CO)—N-(carboxyethyl)-Gly] des(B30) human insulin;
N$^{εB29}$—[N—(HOOC(CH$_2$)$_{14}$CO)—N-(carboxyethyl)-Gly] des(B30) human insulin; and
N$^{εB29}$—[N—(HOOC(CH$_2$)$_{14}$CO)—N-(carboxymethyl)-β-Ala]des(B30) human insulin.

24. b. The long-acting or ultra-long-acting insulin for use according to embodiment 22 a. or b. or 23 a. or b. wherein said insulin is LysB29(Nε-hexadecandioyl-γ-Glu) des(B30) human insulin (insulin degludec, Tresiba®).

25. The long-acting or ultra-long-acting insulin for use according to any one of the preceding embodiments wherein said insulin is administered, either concurrently or consecutively, together with a one or more additional drug used in the treatment of diabetes.

26. The long-acting or ultra-long-acting insulin for use according to embodiment 25 wherein the one or more additional drug used in the treatment of diabetes is, or includes, a drug selected from the group consisting of: insulins, sensitizers such as biguanides and thiazolidinediones, secretagogues such as sulfonylureas and nonsulfonylurea secretagogues, alpha-glucosidase inhibitors and peptide analogs such as injectable incretin mimetics, gastric inhibitory peptide analogs, dipeptidyl peptidase-4 inhibitors and injectable amylin analogues.

27. The long-acting or ultra-long-acting insulin for use according to embodiment 26 wherein the one or more additional drug used in the treatment of diabetes is, or includes, a rapid-acting insulin.

28. The long-acting or ultra-long-acting insulin for use according to embodiment 27 wherein the one or more additional drug used in the treatment of diabetes is, or includes, a rapid-acting insulin selected from the group consisting of insulin aspart, insulin gluisine and insulin lispro.

29. The long-acting or ultra-long-acting insulin for use according to any one of the preceding embodiment wherein said insulin is formulated together with a pharmaceutically acceptable carrier, vehicle, diluent and or excipient.

30. The long-acting or ultra-long-acting insulin for use according to any one of embodiments 28 and 29 wherein said insulin and the one or more additional drug used in the treatment of diabetes is administered concurrently in the same formulation 31. The long-acting or ultra-long-acting insulin for use according to embodiment 25 wherein said insulin is LysB29(N-hexadecandioyl-γ-Glu) des(B30) human insulin (insulin degludec, Tresiba®) and said insulin is administered, concurrently or consecutively, with liraglutide.

32. The long-acting or ultra-long-acting insulin for use according to any one of the preceding embodiments wherein the a disease or condition where administration of insulin will be of benefit is selected from the group consisting of diabetes mellitus such as type 1 diabetes mellitus or type 2 diabetes mellitus, other conditions characterised by hyperglycaemia such as pre-diabetes, impaired glucose tolerance, metabolic syndrome, obesity, cachexia, in vivo beta-cell loss/death, excessive appetite and inflammation.

33. The long-acting or ultra-long-acting insulin for use according to any one of the preceding embodiments wherein the disease or condition where administration of insulin will be of benefit is type 1 diabetes mellitus.

34. The long-acting or ultra-long-acting insulin for use according to any one of the preceding embodiments wherein the disease or condition where administration of insulin will be of benefit is type 2 diabetes mellitus.

35. The long-acting or ultra-long-acting insulin as defined herein in anyone of embodiments 23a., 23b., 24a. and 24b., such as insulin degludec, for use in treating type 1 or type 2 diabetes mellitus, wherein the administration of said insulin comprises or consists of the following steps:
    (a) optionally providing a (optionally capillary) fasting blood or plasma sample from an individual in need of treatment with said insulin, on a given day;
    (b) taking a single fasting self-measured blood or plasma glucose measurement from the sample provided in step (a), on the same day as step (a);
    (c) using the single fasting blood or plasma glucose measurement of step (b) to determine, on the same day as steps (a) and (b), the dose of said insulin to be administered to said individual;
    (d) administering said insulin to said individual at the dose determined in step (c), starting on the same day as steps (a) to (c) and for an administration period of 7 days or of between 6 and 8 days or of between 5 and 9 days; and
    (e) on the day following the last day of the period of administration of step (d), repeating steps (a) to (c) on the same day, then (d) again starting on the same day as (a) to (c) and for another administration period of 7 days or of between 6 and 8 days or of between 5 and 9 days, wherein steps (a) to (d) can so be repeated as long as needed by said individual.

36. A method of treating a disease or condition where administration of a long-acting or ultra-long-acting insulin will be of benefit, comprising or consisting of the following steps:
    (a) optionally providing a blood or plasma sample to be tested from an individual in need of treatment;
    (b) taking a single fasting blood or plasma glucose measurement from said individual in need of treatment;
    (c) using the single fasting blood or plasma glucose measurement to determine the long-acting or ultra-long-acting insulin dose to be administered; and
    (d) administering the long-acting or ultra-long-acting insulin to the individual at the dose determined in step (c).

37. A method of determining a long-acting or ultra-long-acting insulin dose to be administered to an individual suffering from a disease or condition where administration of insulin will be of benefit comprising or consisting of the following steps:
    (a) optionally providing a blood or plasma sample to be tested from an individual in need of treatment;
    (b) taking a single fasting blood or plasma glucose measurement from said individual in need of treatment; and
    (c) using the single fasting blood or plasma glucose measurement to determine the insulin dose to be administered.

38. A kit for use of a long-acting or ultra-long-acting insulin as defined is any of embodiments 1 to 35, a method of treating a disease or condition as defined in embodiment 36 or a method of determining an insulin dose as defined in embodiment 37, comprising or consisting of one or more of the following:
    A) apparatus for providing a blood sample to be tested from an individual in need of treatment;
    B) apparatus for measuring fasting blood glucose;
    C) an insulin as defined in any one of embodiments 1 to 35;
    D) optionally one or more drug used in the treatment of diabetes defined in any one of embodiments 26 to 28; and/or
    E) instructions for performing the administration regime or for using said long-acting or ultra-long-acting insulin as defined in any one of embodiments 1 to 35, the method of treating a disease or condition as defined in embodiment 36 or the method of determining a long-acting or ultra-long-acting insulin dose as defined in embodiment 36.

39. A kit adapted for implementing the use of a long-acting or ultra-long-acting insulin as defined is any of embodiments 1 to 35, a method of treating a disease or condition as defined in embodiment 36 or a method of determining an insulin dose as defined in embodiment 37.

40. A computer and/or a mechanically-implemented kit adapted for implementing the use of a long-acting or ultra-long-acting insulin as defined is any of embodiments 1 to 35, a method of treating a disease or condition as defined in embodiment 36 or a method of determining an insulin dose as defined in embodiment 37.

41. Kits comprising a blood glucose testing apparatus adapted for calculating dosage according to the use of a long-acting or ultra-long-acting insulin as defined is any of embodiments 1 to 35, a method of treating a disease or condition as defined in embodiment 36 or a method of determining an insulin dose as defined in embodiment 37.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention will now be described in more detail with the aid of the following Figures and Examples.

FIG. 1: BEGIN™ Once Simple participant flow

*IDeg$_{Simple}$: arthralgia and blurred vision (1 subject); toxicity to various agents (1 subject); astrocytoma (1 subject); acute myocardial infarction (1 subject).

IDeg$_{Step-wise}$: liver metastases (1 subject); intervertebral disc protrusion (1 subject); worsening of type 2 diabetes/vitamin D deficiency/anterior pituitary disorder/depression (1 subject). †IDeg$_{Simple}$: withdrawal of consent (2 subjects), investigator decision to withdraw subject due to safety or non-compliance (2 subjects), randomized in error (1 subject). IDeg$_{Step-wise}$: withdrawal of consent (2 subjects), investigator decision to withdraw subject due to safety or non-compliance (1 subject), randomized in error (4 subjects). ‡IDeg$_{Simple}$: lost to follow-up (2 subjects) and withdrawn after 11.7 weeks of treatment due to HbA$_{1c}$ increased (1 subject) IDeg$_{Step-wise}$: lost to follow-up (3 subjects). FAS full analysis set, SAS safety analysis set, AE adverse event, IDeg insulin degludec.

Figure 2:
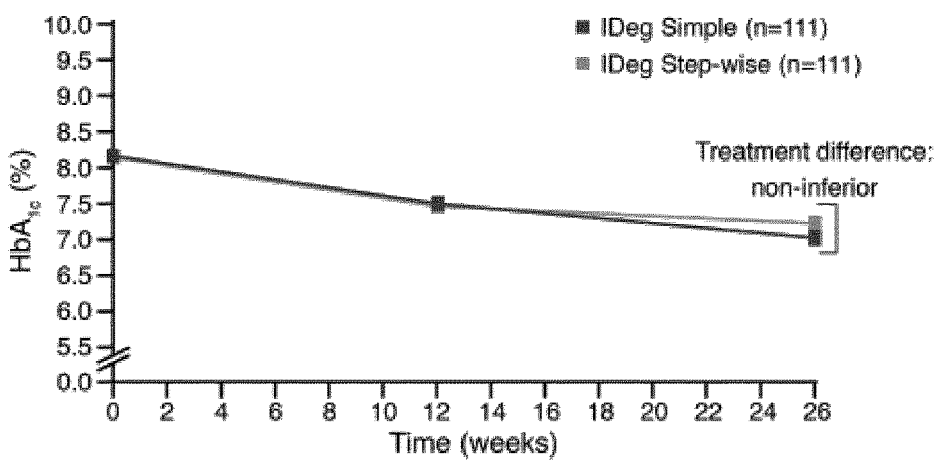
Figure 2:
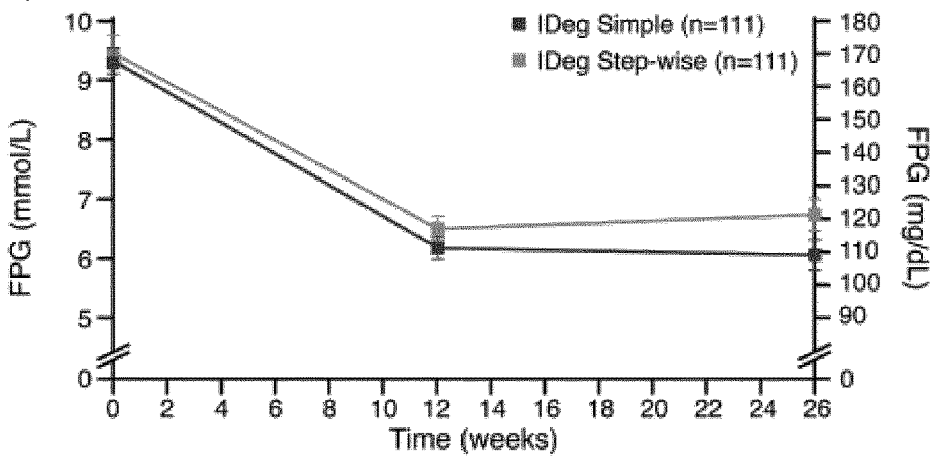
Figure 2:
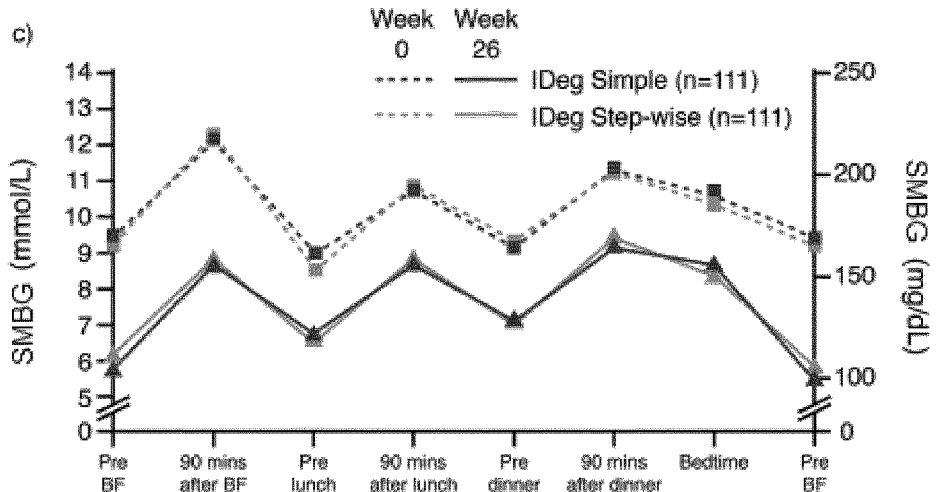

FIG. 2: BEGIN™ Once Simple glycemic efficacy: (a) mean HbA$_{1c}$±SEM over time; (b) mean FPG±SEM over time; (c) 8-point SMBG profile at baseline and Week 26 SEM standard error of the mean, FAS full analysis set, IDeg insulin degludec, FPG fasting plasma glucose, SMBG self-measured blood glucose.

Figure 3:
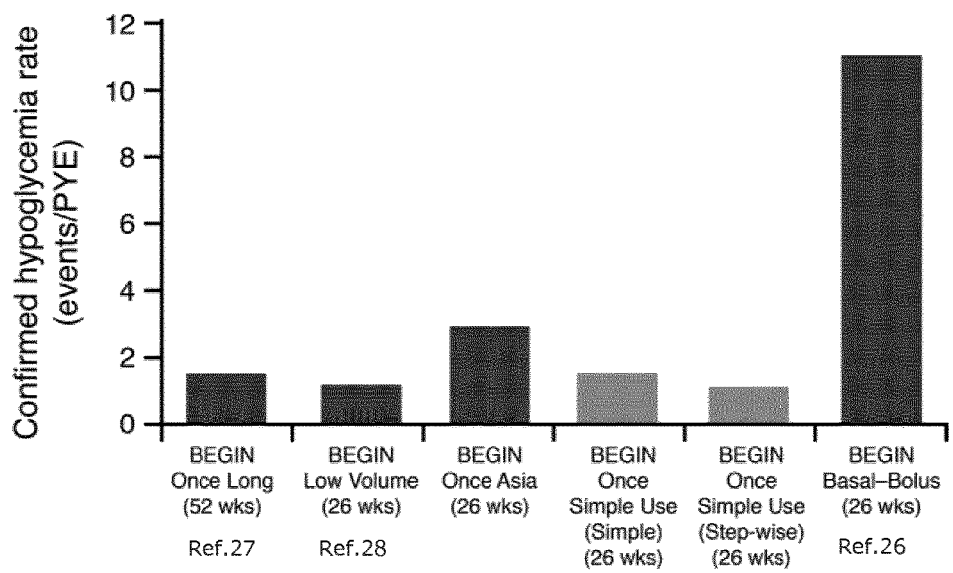
Figure 3:
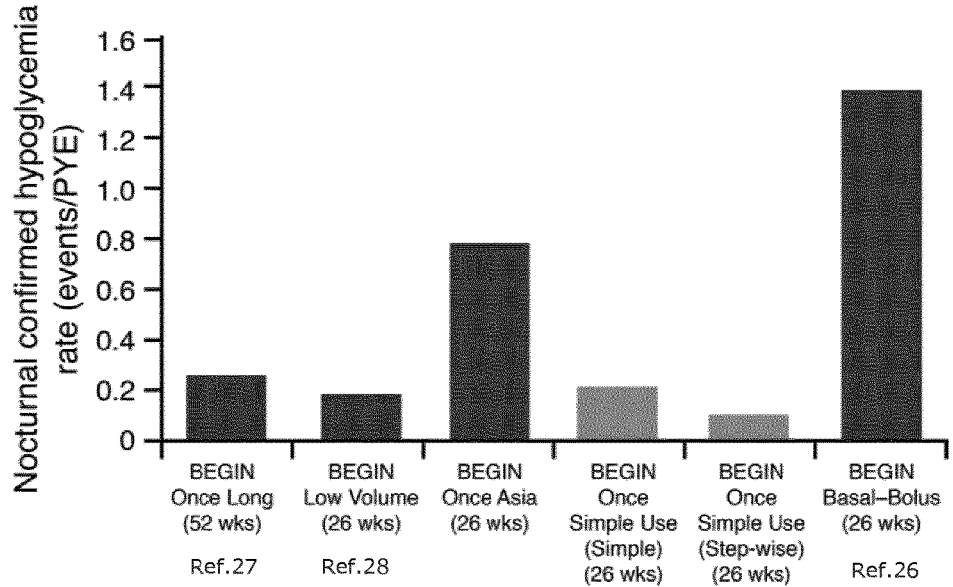

FIG. 3 Hypoglycemia rate (IDeg) in the BEGIN™ Type 2 diabetes trials: (a) Confirmed hypoglycemia (b) Nocturnal confirmed hypoglycemia Rate (events/patient year of exposure) is at end-of-trial and based on SAS. SAS statistical analysis set, IDeg insulin degludec.

EXAMPLES

Example 1—Insulin Degludec Once-Daily in Type 2 Diabetes: Simple or Step-Wise Titration (Begin™: Once Simple Use)

Abstract
Introduction:
Insulin degludec (IDeg) is a new basal insulin in development with a flat, ultra-long action profile that may permit dosing using a simplified titration algorithm with less frequent self-measured blood glucose (SMBG) measurements and more simplified titration steps than currently available basal insulins.

Methods:
This 26-week, multi-center, open-label, randomized, treat-to-target study compared the efficacy and safety of IDeg administered once daily in combination with metformin in insulin-naïve subjects with type 2 diabetes using two different patient-driven titration algorithms: a "Simple" algorithm (IDeg$_{Simple}$), with dose adjustments based on one pre-breakfast SMBG measurement (N=111) versus a "Step-wise" algorithm (IDeg$_{Step-wise}$), with adjustments based on three consecutive pre-breakfast SMBG values (N=111). IDeg was administered using the FlexTouch® insulin pen (Novo Nordisk A/S, Bagsværd, Denmark), with once-weekly dose titration in both groups.

Results:
Glycosylated hemoglobin decreased from baseline to Week 26 in both groups (~1.09%, IDeg$_{Simple}$; −0.93%, IDeg$_{Step-wise}$). IDeg$_{Simple}$ was non-inferior to IDeg$_{Step-wise}$ in lowering HbA$_{1c}$ (estimated treatment difference [IDeg$_{Simple}$-IDeg$_{Step-wise}$]: −0.16%-points [−0.39; 0.07]$_{95\% CI}$). Fasting plasma glucose was reduced (~3.27 mmol/L, IDeg$_{Simple}$; −2.68 mmol/L, IDeg$_{Step-wise}$) with no significant difference between groups. Rates of confirmed hypoglycemia (1.60, IDeg$_{Simple}$; 1.17, IDeg$_{Step-wise}$ events/patient year of exposure [PYE]) and nocturnal confirmed hypoglycemia (0.21, IDeg$_{Simple}$; 0.10, IDeg$_{Step-wise}$ events/PYE) were low, with no significant differences between groups. Daily insulin dose after 26 weeks was 0.61 U/kg (IDeg$_{Simple}$) and 0.50 U/kg (IDeg$_{Step-wise}$). No significant difference in weight change was seen between groups by Week 26 (+1.6 kg, IDeg$_{Simple}$; +1.1 kg, IDeg$_{Step-wise}$), and there were no clinically relevant differences in adverse event profiles.

Conclusion:
IDeg was effective and well tolerated using either the Simple or Step-wise titration algorithm. While selection of an algorithm must be based on individual patient characteristics and goals, the ability to attain good glycemic control using a simplified titration algorithm may enable patient empowerment through self-titration, improved convenience, and reduced costs.

Introduction
Numerous studies investigating the cost of self-measured blood glucose (SMBG) testing have found that it comprises a substantial portion of diabetes-related expenditures [15-18]. In a retrospective database analysis in the US that included more than 45,000 patients, testing accounted for 27% of diabetes care costs: total combined blood glucose testing and insulin-related costs were $2,850 USD/patient/year, with $772 USD/patient/year attributed to blood glucose testing alone [18]. In other countries, testing comprises an even higher percentage of diabetes care costs, (e.g., 40% in Canada [16, 17] and 42% in Germany [15]).

Insulin degludec (IDeg) is a new basal insulin (currently approved in Europe, Japan, Mexico and several other countries) with a flat, ultra-long action profile that may enable subjects to achieve glycosylated hemoglobin (HbA$_{1c}$) levels closer to glycemic target with fewer hypoglycemic episodes [19-21]. It was thus hypothesized that IDeg could be titrated once weekly based on a single pre-breakfast SMBG value, offering a simple, patient-focused titration algorithm that would encourage self-titration, enhancing patient empowerment as well as substantially reducing treatment costs by reducing the frequency of blood glucose measurements required for dose adjustments. In this study, after 26 weeks of treatment, we compared the efficacy and safety of two different self-titration algorithms for IDeg administered once daily (OD) plus metformin, in insulin-naïve subjects with type 2 diabetes: a "Simple" algorithm, in which 4 unit [U] dose adjustments were made based on a single pre-breakfast SMBG measurement was compared with a "Step-wise" algorithm, in which dose adjustments were made in increments of 2 U (Table 2) based on the lowest of three consecutive pre-breakfast SMBG readings. In both groups, IDeg was adjusted once weekly. The objective of this trial was to provide additional guidance on the use of IDeg in clinical practice by investigating whether good glycemic control could be attained with a more simplified titration schedule, involving fewer SMBG tests, than that previously employed during the IDeg Phase 3a development program.

Methods
The study was conducted according to the Declaration of Helsinki (2008) [22] and ICH Good Clinical Practice (1996) guidelines [23], with prior approval by appropriate ethics committees and patient consent obtained in writing prior to the start of any study-related activities. Eligible participants included insulin-naïve men or women ≥18 years of age, with type 2 diabetes, HbA$_{1c}$ 7.0-10.0% (inclusive), and body mass index (BMI)≤45.0 kg/m², who were treated with ≥1000 mg/day metformin alone or in combination with one or two other oral antidiabetic medications (OADs) (including a sulfonylurea [SU] or glinide, dipeptidyl peptidase-4 [DPP-4] inhibitors, α-glucosidase inhibitors or thiazolidinediones [TZDs]), with unchanged dosing for ≥12 weeks prior to randomization. Participants were ineligible if they had used a glucagon-like-peptide-1 (GLP-1) receptor agonist within 12 weeks prior to randomization; had initiated or significantly changed treatment that could interfere with glucose metabolism; had significant disease other than type 2 diabetes; were pregnant or breastfeeding; or had recurrent severe hypoglycemia/hypoglycemia unawareness. Subjects could be withdrawn from the trial due to withdrawal of consent, not fulfilling inclusion/exclusion criteria (randomized in error), non-compliance, or at the discretion of the investigator due to a safety concern. Subjects who were withdrawn after randomization were not to be replaced. This trial is registered at clinicaltrials.gov: NCT01326026.

Study Design and Treatment

This was a multinational (conducted in the US, Spain, Finland, and Germany), Phase 3b, multi-center, two-armed, parallel group, open-label, randomized, treat-to-target study that compared the efficacy and safety of IDeg OD [IDeg 100 U/mL, FlexTouch® pen, Novo Nordisk A/S, Bagsværd, Denmark], adjusted using two different titration algorithms in combination with metformin. The trial consisted of a 26-week period; total study duration was approximately 28 weeks (including 1 week for screening and a 7-day follow-up period). After discontinuing all OADs other than metformin, subjects were randomized 1:1 by an interactive voice/web response system (IV/WRS) to $IDeg_{Simple}$ or $IDeg_{Step-wise}$ insulin self-titration algorithms, as defined below. Subjects were instructed to self-titrate in accordance with their respective algorithms and continue with their pre-trial metformin dose. At randomization, Week 4 and Week 12, subjects in both treatment arms received diet and exercise counselling by an HCP. The importance of maintaining a healthy diet and exercise plan was reinforced at each visit.

A Novo Nordisk A/S safety committee blinded to treatment performed on-going safety surveillance, but could request unblinding of the data to be performed by an independent ad hoc group, if needed. Blinded insulin titration surveillance was performed by Novo Nordisk A/S.

IDeg was administered OD at a starting dose of 10 U in both groups. Variation of injection time from day to day was permitted, as long as subjects maintained a minimum of 8 and a maximum of 40 hours between injections. Self-adjustment of IDeg dose was to be performed once weekly in both groups according to the algorithms outlined in Table 2. In the $IDeg_{Simple}$ arm, dose adjustment was based on a single pre-breakfast SMBG measurement. In the $IDeg_{Step-wise}$ arm, dose adjustment was based on the lowest of 3 consecutive days' pre-breakfast SMBG measure.

Efficacy and Safety Assessments $HbA_{1c}$ was analyzed using a Bio-Rad high-performance liquid chromatography method at Visits 1 (screening), 2 (randomization), 14 (Week 12) and 28 (Week 26).

Fasting plasma glucose (FPG) blood samples were assayed using a hexokinase-UV method at Visits 2, 14 and 28. At the first visit, subjects were provided with a glucose meter for SMBG measurement and instructions for use; blood glucose was measured with test strips calibrated to plasma glucose to obtain PG-equivalent values presented in this report. Subjects performed SMBG measurements before breakfast weekly after randomization and also performed an 8-point SMBG profile prior to Visits 2, 14 and 28.

Adverse events (AEs) and hypoglycemic episodes were documented throughout the study, with confirmed hypoglycemia defined as episodes of severe hypoglycemia (requiring assistance from another person) and episodes with PG value <3.1 mmol/L (56 mg/dL). Nocturnal confirmed hypoglycemic episodes were those occurring between 00:01 h and 05:59 h (inclusive). Laboratory safety variables, insulin dose and body weight were recorded at pre-specified intervals. Two patient-reported outcome (PRO) questionnaires (Device-Specific questionnaires I and II) were self-completed at Visits 14 and 28 to assess subject satisfaction with the FlexTouch® pen as an additional trial endpoint. The PRO questionnaire utilized here to assess patient satisfaction with FlexTouch® had previously been used in other trials to assess satisfaction with the FlexPen® device (Novo Nordisk A/S, Bagsværd, Denmark) [24, 25].

Statistical Methods

With 218 subjects, there was 85% power to demonstrate non-inferiority at 0.4% in evaluation of the per-protocol (PP) analysis set (defined as all subjects without major protocol violations who were exposed to treatment for >12 weeks and who had a valid assessment necessary for deriving the primary endpoint), accounting for an anticipated total of 15% that would not be included in the PP analysis set. Sample size was determined using a t-statistic under the assumption of a one-sided test of size 2.5% and a zero mean treatment difference. Data were reported using a 95% confidence interval (CI) and P-values for 1-sided testing for non-inferiority at alpha=0.025 for the primary analysis, and 2-sided testing with alpha=0.050 for all other analyses. Statistical analyses of all efficacy and patient-reported outcome endpoints were based on the full analysis set (FAS), defined as all randomized subjects, and followed the intention-to-treat (ITT) principle unless otherwise noted. The robustness of the results for change in $HbA_{1c}$ was explored by an additional analysis of the PP analysis set. Further, robustness was explored by an additional analysis of the set of all subjects who completed the trial and by using a simple model based on the FAS with only treatment and baseline $HbA_{1c}$ as covariates. Safety endpoints were summarized based on the safety analysis set (SAS), defined as all subjects who received at least one dose of IDeg, and analyzed based on the FAS.

Change from baseline in $HbA_{1c}$ after 26 weeks was analyzed using an analysis of variance (ANOVA) method with treatment, region, sex and antidiabetic therapy at screening as fixed factors, and age and baseline $HbA_{1c}$ as covariates. Non-inferiority was considered confirmed if the upper bound of the two-sided 95% CI for the treatment difference ($IDeg_{Simple}$-$IDeg_{Step-wise}$) for the mean change in $HbA_{1c}$ was 50.4%. Change in FPG and change in body weight were analyzed using an ANOVA model similar to that used for the primary analysis, but with the relevant baseline value as covariate for each measure. Responder endpoints (proportion of subjects who achieved target $HbA_{1c}$ and proportion who achieved target without hypoglycemia) were analyzed using a logistic regression model with the same factors and covariates as those used for the primary analysis. An 8-point SMBG profile included measurements before and 90 minutes after the start of breakfast, lunch and main evening meal, prior to bedtime, and before breakfast the following day. A mixed effect model including treatment, time, interaction between treatment and time, antidiabetic therapy at screening, sex and region as fixed factors, age as covariate and subject as random effect was fitted to the 8-point SMBG profile data. From this model, mean profile by treatment and relevant treatment differences were estimated and explored. Treatment-emergent AEs, hypoglycaemic episodes, laboratory parameters, physical examination, electrocardiogram (ECG), fundoscopy/fundusphotography, vital signs, PRO (Device-Specific questionnaires I and II) and insulin dose were summarized with descriptive statistics. The numbers of treatment-emergent confirmed and nocturnal confirmed hypoglycaemic episodes were analyzed using a negative binomial regression model with a log-link function and the logarithm of the time period for which a hypoglycaemic episode was considered treatment emergent as offset; the model included treatment, sex, region and antidiabetic treatment at screening as fixed factors and age as covariate.

Results

Demographics and Baseline

Participants were allocated 1:1 to the IDeg$_{Simple}$ (N=111) and IDeg$_{Step-wise}$ (N=111) arms (Table 3). Of 222 randomized participants, 221 (99.5%) received trial drug. Treatment arms were well matched at baseline, with the exception of a slightly higher mean body weight and more female subjects in the IDeg$_{Simple}$ arm. Subjects in the IDeg$_{Step-wise}$ arm had a slightly longer mean duration of diabetes. The majority of participants in both groups were taking two OADs at baseline (61/111 subjects, 55%); ~21% in each group were taking >2 OADs, and ~24% in each group were taking 1 OAD. The most common pre-trial OAD other than metformin was a SU. Most (89.2% [99/111], IDeg$_{Simple}$; 88.3% [98/111], IDeg$_{Step-wise}$) subjects completed the trial. Four IDeg$_{Simple}$ and three IDeg$_{Step-wise}$ subjects were withdrawn due to AEs; five IDeg$_{Simple}$ and seven IDeg$_{Step-wise}$ subjects were withdrawn due to meeting withdrawal criteria; and three subjects in each group were withdrawn due to reasons classified as "other" (FIG. 1).

HbA$_{1c}$ decreased from baseline to Week 26 in both groups; −1.09% with IDeg$_{Simple}$, to 7.0%, and −0.93% with IDeg$_{Step-wise}$, to 7.2% (FIG. 2a). IDeg$_{Simple}$ was non-inferior to IDeg$_{Step-wise}$ in lowering HbA$_{1c}$, as the upper limit of the 95% CI for the estimated treatment difference (ETD) was <0.4%: ETD (IDeg$_{Simple}$-IDeg$_{Step-wise}$) −0.16%-points [−0.39; 0.07]$_{95}$% CI. Analyses to measure robustness of results were consistent with FAS results. Significantly more IDeg$_{Simple}$ (56.8% [63/111]) than IDeg$_{Step-wise}$ (41.4% [46/111]) subjects achieved HbA$_{1c}$<7.0% at end-of-trial; estimated odds ratio (IDeg$_{Simple}$/IDeg$_{Step-wise}$): 1.93 [1.04; 3.55]$_{95\% CI}$ (P=0.0356). There was no significant difference in the proportion of patients achieving HbA$_{1c}$<7% without confirmed hypoglycemia (40.6% [43/106] IDeg$_{Simple}$; 34.6% [36/104] IDeg$_{Step-wise}$); estimated odds ratio (IDeg$_{Simple}$/IDeg$_{Step-wise}$): 1.26 [0.69; 2.29]$_{95\% CI}$.

FPG decreased from baseline to Week 26 by 3.27 mmol/L with IDeg$_{Simple}$, to 6.1 mmol/L, and by 2.68 mmol/L with IDeg$_{Step-wise}$, to 6.8 mmol/L (FIG. 2b). No significant difference was seen between groups: ETD (IDeg$_{Simple}$-IDeg$_{Step-wise}$): −0.57 mmol/l [−1.30; 0.17]$_{95}$% CI. The most pronounced decline in FPG occurred during the first 12 weeks. No difference between groups in 8-point SMBG profiles was seen at any of the eight measured time points at baseline or at end-of-trial (FIG. 2c).

Rates of confirmed hypoglycemia were low, at 1.60 and 1.17 events per patient year of exposure (PYE) with IDeg$_{Simple}$ and IDeg$_{Step-wise}$, respectively (FIG. 3a), with no significant difference between groups (P=0.4273). One severe hypoglycemic episode occurred in the IDeg$_{Simple}$ arm 5 days after the last treatment with IDeg. Observed rates of nocturnal confirmed hypoglycemia were very low at 0.21 (IDeg$_{Simple}$) and 0.10 (IDeg$_{Step-wise}$) events per PYE (FIG. 3b), with no significant difference between groups (P=0.2047).

The observed daily insulin dose after 26 weeks was 62 U (0.61 U/kg) in the IDeg$_{Simple}$ arm and 48 U (0.50 U/kg) in the IDeg$_{Step-wise}$ arm. Up to Week 4, mean doses were similar, after which the mean dose in the Simple arm was higher. The increase in IDeg dose per week began to level off in the IDeg$_{Step-wise}$ arm at Week 14. Although subjects were permitted to adjust their dose by increments larger than 4 U in the IDeg$_{Step-wise}$ arm, the mean weekly incremental increase was ≤3 U.

Mean baseline body weight was higher in the IDeg$_{Simple}$ arm (95.7 kg) than in the IDeg$_{Step-wise}$ arm (91.3 kg). Modest increases in weight were observed from baseline to Week 26 in both groups: IDeg$_{Simple}$: (+1.6 kg, to mean weight 97.3 kg at Week 26), IDeg$_{Step-wise}$ (+1.1 kg, to mean weight 92.4 kg at Week 26), with no statistically significant difference in weight change: ETD (IDeg$_{Simple}$-IDeg$_{Step-wise}$) 0.46 kg [−0.35; 1.26]$_{95\% CI}$. There were no clinically relevant differences from baseline to end-of-trial or between treatment arms for vital signs, ECG, fundoscopy, physical examination or laboratory parameters (data not shown).

No safety concerns were raised during this trial. Please see Table 4 for an overview of the rates of AEs and serious AEs (SAEs) reported. AEs and SAEs were distributed similarly between groups. Most AEs were of mild or moderate severity and the rates of AEs classified as possibly or probably related to trial product by the investigator were low (10.0% [IDeg$_{Simple}$]; 7.2% [IDeg$_{Step-wise}$]). Injection-site reactions (ISRs) were reported by 2.7% (3 subjects with 3 events) of IDeg$_{Simple}$ and 4.5% (5 subjects with 16 events) of IDeg$_{Step-wise}$ subjects; one subject reported 9 of the 16 total events in the IDeg$_{Step-wise}$ arm, and reported "pain" as the ninth ISR. No SAEs were reported in ≥5% of subjects and none were considered by the investigator to be related to trial product. One death occurred in this study 154 days after starting trial drug in an IDeg$_{Step-wise}$-treated participant, due to liver metastasis (the primary cancer was reported as probable small cell lung carcinoma). The event was considered by the investigator to be unlikely related to treatment. One other SAE neoplasm event (astrocytoma [IDeg$_{Simple}$]), and three events adjudicated as major adverse cardiovascular events (coronary artery stenosis [IDeg$_{Simple}$], acute myocardial infarction [IDeg$_{Simple}$] and coronary artery occlusion [IDeg$_{Step-wise}$]) occurred, all of which were considered by the investigator to be unlikely related to treatment. No IDeg-related medication errors were reported.

In the Device-Specific questionnaires, more than 90% of subjects at Week 12 and Week 26 indicated the highest levels of satisfaction (response category 1 or 2) with the FlexTouch® device. At 26 weeks, 98% of subjects reported no problems using FlexTouch® and 100% of subjects indicated that they would recommend the pen. Please refer to Table 5 for additional details on the results of the questionnaires (Table 5 contains a subset of the total questions surveyed in this trial).

Discussion

Both the Simple and Step-wise titration algorithms were effective, well-tolerated methods of achieving glycemic targets with IDeg, thereby demonstrating that titration based on either a single weekly SMBG measurement with the Simple algorithm, or three measurements with the Step-wise algorithm, provide suitable options for patients with type 2 diabetes. Titration using the Simple algorithm was shown to be non-inferior to titration using the Step-wise algorithm in terms of improving HbA$_{1c}$ and both methods resulted in a similar FPG reduction. End-of-trial HbA$_{1c}$ and change from baseline in HbA$_{1c}$ in both treatment arms were similar to values seen with IDeg in similar previous Phase 3a (BEGIN™) trials in people with type 2 diabetes. These previous trials all demonstrated similar efficacy between IDeg and insulin glargine as demonstrated by non-inferiority in terms of change in HbA$_{1c}$, were 26 or 52 weeks in duration, enrolled insulin-naïve subjects (except for the BEGIN™

Basal-Bolus T2 study in which insulin aspart was dosed with meals [26]) and employed a titration algorithm similar to the Step-wise algorithm, but with weekly titration based on the mean of 3 consecutive days' pre-breakfast SMBG measurements [26-29].

IDeg dose was increased more quickly in the IDeg Simple arm, whereas insulin dose escalation was reduced earlier in the IDeg$_{Step\text{-}wise}$ arm, reflecting a point of differentiation between the algorithms: as pre-breakfast SMBG values approached target, the Step-wise algorithm permitted a smaller dose increase of 2 U versus the recommended 4 U increase in the IDeg$_{Simple}$ arm. Insulin dose was higher at end-of-trial in the IDeg$_{Simple}$ arm than in the IDeg$_{Step\text{-}wise}$ arm, which may account for the non-significant differences seen between groups in FPG and hypoglycemia. FPG values were numerically lower over longer periods of time in the IDeg Simple arm; this may have influenced the observed rates of hypoglycemia, as these rates represented the entire treatment period. The small and non-significant difference in FPG between the IDeg$_{Simple}$ and IDeg$_{Step\text{-}wise}$ arms likely also contributed to the difference between groups in achieving the HbA$_{1c}$ target of <7%. It is important to note that there was no significant difference between groups in the achievement of the HbA$_{1c}$ target without confirmed hypoglycemia.

The Simple algorithm offers an easy and patient-friendly way to titrate IDeg; additionally, the capacity to adjust IDeg doses with a 4 U increase or decrease, based on a single weekly SMBG value, may substantially reduce the financial and time burden and inconvenience of titration measurements. Incidence rates of hypoglycemic episodes were very low, with no significant difference between the Simple and Step-wise arms. As shown in FIG. 3a and FIG. 3b, respectively, end-of-trial confirmed and nocturnal confirmed hypoglycemia rates seen here were comparable to or lower than rates with IDeg administered OD in the BEGIN™ trials in people with type 2 diabetes; rates that, in turn, were lower than or similar to those seen with comparator insulin glargine in other studies of the insulin degludec development program. [26-29]

Subjects in both treatment arms adhered closely to their respective algorithms. The ability and willingness of patients to adhere to a given treatment regimen is an important component in the success of insulin therapy. Surveys of physicians and patients have identified "too busy" and "complicated regimen" as prominent reasons why patients miss or omit insulin injections; 17% of patients report difficulty in adjusting insulin doses, and 60% of patients feel that their insulin regimens can be restrictive [10-11]. There is evidence to support the premise that if patients are more comfortable with, and accepting of, their dosing regimen, they may be more willing to continue treatment in the long-term [12-14]. Furthermore, patient empowerment may be enhanced by a titration algorithm that facilitates self-adjustment of basal insulin and better adherence to treatment regimens, potentially leading to improved health outcomes. In the Predictable Results and Experience in Diabetes through Intensification and Control to Target: An International Variability Evaluation (PREDICTIVE™) 303 study with insulin detemir, a simplified self-adjusted dosing algorithm in which patients tested SMBG daily and adjusted their dose every 3 days based on the mean of the previous 3 days' values was shown to significantly lower HbA$_{1c}$ versus standard-of-care, physician-driven adjustments over a period of 6 months [4], thus, providing further evidence that a simple self-titration method can help subjects achieve glycemic targets. Additionally, patient acceptance of the insulin delivery device used to administer doses is a factor that appears to influence adherence and persistence with a given treatment regimen [30-33]. It has been reported that positive perceptions of convenience also play an important role in the persistence of pen use [34]. In this trial, high levels of satisfaction with the FlexTouch® insulin pen device were reported in both treatment arms and all subjects indicated that they would recommend the pen to others. This reflects the experiences of patients in other IDeg trials using the same device, in which the majority of patients reported ease in using the pen and a high degree of satisfaction with FlexTouch® [35-39].

Conclusion

Achieving good glycemic control in patients with type 2 diabetes is an important way to prevent or limit diabetes complications, and control the costs of intensified healthcare utilization stemming from these complications. SMBG is an integral part of effective diabetes management; however, glucose meters, test strips, lancets, and alcohol wipes are consumable items that comprise on-going expenses, with test strips identified as a major driver of these costs [15-18]. New medications and treatment regimens that permit a reduction in the number of SMBG measurements without compromising clinical outcomes would likely benefit all basal insulin-treated patients who may find current algorithms confusing or cumbersome. These patients may be more likely to adhere to a simpler regimen that ultimately results in improved health outcomes and lower healthcare costs. This trial demonstrates that IDeg, titrated using either the Simple or Step-wise algorithm, leads to good glycemic control and is well tolerated, offering individualized titration regimens that best meet patient needs.

Example 2—Assay (I): Insulin Receptor Binding

The affinity of the insulin-like compounds for use in the present invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl was then added and a dilution series is made from appropriate samples. To the dilution series was then added 100 µl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Example 3—Assay (11): Potency of the Insulin Derivatives of the Invention Relative to Human Insulin Sprague Dawley male rats weighing 238-383 g on the experimental day were used for the clamp experiment. The rats had free access to feed under controlled ambient conditions and were fasted overnight (from 3 pm) prior to the clamp experiment.

Experimental Protocol:

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorised and fixed on the back of the neck. The rats were given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 pm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Test compounds and doses: Insulin-like compounds for use in the present invention to be tested were diluted from a stock solution containing 97 µM of the insulin derivative in 5 mM phosphate pH 7.7. The final concentration in the solution ready for use was 0.45 µM of the insulin derivative, 5 mM of phosphate, 100 mM of sodium chloride, 0.007% of polysorbate 20. The pH was 7.7 and the i.v. infusion rate was 15 and 20 pmol·min$^{-1}$·kg$^{-1}$.

A stock solution of human insulin that was used as reference compound was formulated in a similar medium and infused i.v. at 6, 15 or 30 pmol·min$^{-1}$·kg$^{-1}$.

Both stock solutions were stored at −20° C. and thawed overnight at 4 OC before use. The solutions were gently turned upside down several times 15 min before they were transferred to the infusion syringes.

REFERENCES

1. American Diabetes Association. Standards of Medical Care in Diabetes—2012. Diabetes Care. 2012; 35(Suppl 1):S11-63.
2. International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.
3. Canadian Diabetes Association Clinical Practice Guidelines Expert Committee. Canadian Diabetes Association. Can J Diabetes. 2008; 32(Suppl 1):S1-201.
4. Meneghini L, Koenen C, Wenig W, Selam J-L. The usage of a simplified self-titration dosing guideline (303 Algorithm) for insulin detemir in patients with type 2 diabetes-results of the randomized, controlled PREDICTIVE™ 303 study. Diabetes Obes Metab. 2007; 9:902-13.
5. Davies M, Storms F, Shutler S, Bianchi-Biscay M, Gomis R. Improvement of glycemic control in subjects with poorly controlled type 2 diabetes. Diabetes Care. 2005; 28:1282-8.
6. LANTUS® (insulin glargine [rDNA origin] injection). Sanofi-Aventis U.S. LLC, Bridgewater, N.J., USA; 2007. Health Care Professional. Dosing & Titration. Available at: http://www.lantus.com/hcp/titration.aspx. Accessed Nov. 13, 2012.
7. Benjamin E M. Self-monitoring of blood glucose: the basics. Clin Diabetes. 2002; 20(1):45-7.
8. Schnell O, Saarlouis H A, Battelino T B, et al. Consensus statement on self-monitoring of blood glucose in diabetes. Diabetes, Stoffwechsel und Herz. 2009; 4:285-9.
9. American Diabetes Association. Insulin administration. Diabetes Care. 2002; 25:S112-15.
10. Peyrot M, Barnett A H, Meneghini L F, Schumm-Draeger P M. Factors associated with injection omission/non-adherence in the Global Attitudes of Patients and Physicians in Insulin Therapy Study. Diabetes Obes Metab. 2012; 14:1081-7.
11. Peyrot M, Barnett A H, Meneghini L F, Schumm-Draeger P M. Insulin adherence behaviours and barriers in the multinational Global Attitudes of Patients and Physicians in insulin therapy study. Diabet Med. 2012; 29:682-90.
12. Norris S L, Lau J, Smith S J, et al. Self-management education for adults with type 2 diabetes: a meta-analysis on the effect of glycemic control. Diabetes Care. 2002; 25:1159-71.
13. Kulzer B, Hermanns N, Reinecker H, Haak T. Effects of self-management training in type 2 diabetes: a randomized, prospective trial. Diabet Med. 2007; 24:415-23.
14. Anderson R M, Funnell M M, Butler P M, et al. Patient empowerment: results of a randomized controlled trial. Diabetes Care. 1995; 18:943-9.
15. Liebl A, Breitscheidel L, Nicolay C, Happich M. Direct costs and health-related resource utilisation in the 6 months after insulin initiation in German patients with type 2 diabetes mellitus in 2006: INSTIGATE study. Curr Med Res Opin. 2008; 24:2349-58.
16. Yeaw J, Christensen T E, Groleau D, Wolden M L, Lee W C. Self-monitoring blood glucose test strip utilization in Canada. Diabetes. 2012; 61(Suppl 1):A35.
17. Yeaw J, Lee W C, Wolden M L, Christensen T, Groleau D. Cost of self-monitoring of blood glucose in Canada among patients on an insulin regimen for diabetes. Diabetes Ther. Epub Jun. 27, 2012. doi: 10.1007/s13300-012-0007-6.
18. Yeaw J, Lee W C, Aagren M, Christensen T J. Cost of self-monitoring of blood glucose in the United States among patients on an insulin regimen for diabetes. J Manag Care Pharm. 2012; 18:21-32.
19. Heise T, Hermanski L, Nosek L, Feldman A, Rasmussen S, Haahr H. Insulin degludec: four times lower pharmacodynamic variability than insulin glargine under steady-state conditions in type 1 diabetes. Diabetes Obes Metab. 2012; 14:859-64.

20. Heise T, Nosek L, Hovelmann U, Bøttcher S G, Hastrup H, Haahr H. Insulin degludec 200 U/mL is ultra-long-acting and has a flat and stable glucose-lowering effect. Diabetes. 2012; 61(Suppl. 1):A91.
21. Korsatko S, Deller S, Zahiragic S, et al. Ultra-long-acting insulin degludec: bio-equivalence and similar pharmacodynamics shown for two different formulations (U100 and U200). Diabetologia. 2011; 54(Suppl. 1):S427.
22. World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Jan. 4, 2013.
23. International Conference on Harmonisation. ICH Harmonised Tripartite Guideline: Guideline for Good Clinical Practice. E6 (R1), Step 4. Oct. 6, 1996. Available at: http://www.ich.org/fileadmin/Public_Web_Site/ICH_Products/Guidelines/Efficacy/E6_R1/Step4/E6_R1 Guideline.pdf. Accessed Jan. 4, 2013.
24. Niskanen L, Jensen L E, Rastam J, Nygaard-Pedersen L, Erichsen K, Vora J P. Randomized, multinational, open-label, 2-period, crossover comparison of biphasic insulin aspart 30 and biphasic insulin lispro 25 and pen devices in adult patients with type 2 diabetes mellitus. Clin Ther. 2004; 26:531-40.
25. Garg S, Bailey T, DeLuzio T, Pollum D. Preference for a new prefilled insulin pen compared with the original pen. Curr Med Res & Opin. 2011; 27:2323-33.
26. Garber A J, King A B, Del Prato S, et al; on behalf of the NN1250-3582 BEGIN™ BB T2D trial investigators. Insulin degludec, an ultra-long acting basal insulin, versus insulin glargine in basal-bolus treatment with mealtime insulin aspart in type 2 diabetes (BEGIN™ Basal-Bolus Type 2): a phase 3, randomised, open-label, treat-to-target non-inferiority trial. Lancet. 2012; 379:1498-507.
27. Zinman B, Philis-Tsimikas A, Cariou B, et al; on behalf of the NN1250-3579 BEGIN™ Once Long trial investigators. Insulin degludec versus insulin glargine in insulin-naïve patients with type 2 diabetes: a 1-year, randomized, treat-to-target trial (BEGIN™ Once Long). Diabetes Care. 2012; 35:2464-71.
28. Bergenstal R, Bhargava A, Jain R K, et al; on behalf of the NN1250-3672 BEGIN™ Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.
29. Onishi Y, Ono Y, Rabl R, Endahl L, Nakamura S. Superior glycaemic control with once-daily insulin degludec/insulin aspart versus insulin glargine in Japanese adults with type 2 diabetes inadequately controlled on oral drugs: a randomized, controlled phase 3 trial. Diabetes Obes Metab. 2013 Mar. 13; doi: 10.1111/dom.12097.
30. Rakel R E. Improving patient acceptance and adherence in diabetes management: a focus on insulin therapy. Adv Ther. 2009; 26:838-46.
31. Ross S A, Tildesley H D, Ashkenas J. Barriers to effective insulin treatment: the persistence of poor glycemic control in type 2 diabetes. Curr Med Res Opin. 2011; 27(Suppl 1):13-20.
32. Reimer T, Hohberg C, Pfützner A H, Jørgensen C, Jensen K H, Pfützner A. Intuitiveness, instruction time, and patient acceptance of a prefilled insulin delivery device and a reusable insulin delivery device in a randomized, open-label, crossover handling study in patients with type 2 diabetes. Clin Ther. 2008; 30:2252-62.
33. Rubin R R and Peyrot M. Factors affecting use of insulin pens by patients with type 2 diabetes. Diabetes Care. 2008; 31:430-2.
34. Peyrot M and Rubin R R. Factors associated with persistence and resumption of insulin pen use for patients with type 2 diabetes. Diabetes Technol Ther. 2011; 13:43-8.
35. Oyer D, Narendran P, Qvist M, Niemeyer M, Nadeau D A. Ease of use and preference of a new versus widely available pre-filled insulin pen assessed by people with diabetes, physicians and nurses. Expert Opin Drug Deliv. 2011; 8:1259-69.
36. Bailey T, Thurman J, Niemeyer M, Schmeisl G. Usability and preference evaluation of a prefilled insulin pen with a novel injection mechanism by people with diabetes and healthcare professionals. Curr Med Res Opin. 2011; 27:2043-52.
37. Nadeau D A, Campos C, Niemeyer M, Bailey T. Healthcare professional and patient assessment of a new pre-filled insulin pen versus two widely available prefilled insulin pens for ease of use, teaching and learning. Curr Med Res Opin. 2012; 28:3-13.
38. Lajara R, Guerrero G, Thurman J. Healthcare professional and patient perceptions of a new prefilled insulin pen versus vial and syringe. Expert Opin Drug Deliv. 2012; 9:1181-96.
39. Bailey T, Campos C. FlexTouch® for the delivery of insulin: technical attributes and perception among patients and healthcare professionals. Expert Rev Med Devices. 2012; 9:209-17.
40. Heise T, Hövelmann U, Noszek L, Bøttcher S, Granhall C, Haahr H. Insulin degludec: two-fold longer half-life and a more consistent pharmacokinetic profile than insulin glargine. Poster presented at EASD Annual Meeting 12-16 Sep. 2011, Lisbon, Portugal.

Tables

TABLE 1

Fluctuation of glucose-lowering effect over 24 hours at steady state

| Dose | Insulin degludec AUCF$_{GIR,\tau}$ | Insulin glargine AUCF$_{GIR,\tau}$ |
| --- | --- | --- |
| 0.4 U/kg | 0.25 mg/kg/min | 0.39 mg/kg/min |
| 0.6 U/kg | 0.37 mg/kg/min | 0.54 mg/kg/min |
| 0.8 U/kg | 0.38 mg/kg/min | 0.73 mg/kg/min |

Data are geometric means. AUCF$_{GIR,\tau}$ = (AUC(above GIR$_{mean}$) + AUC(below GIR$_{mean}$))/24

TABLE 2

Comparison of BEGIN™ Once Simple titration algorithms

| Pre-breakfast SMBG | | Dose adjustment IDeg Simple[a] | Dose adjustment IDeg Step-wise[b] |
| --- | --- | --- | --- |
| mmol/L | mg/dL | U | U |
| <3.1 | <56 | −4 | −4 |
| 3.1-3.9 | 56-70 | | −2 |
| 4.0-5.0 | 71-90 | 0 | 0 |
| 5.1-7.0 | 91-126 | +4 | +2 |
| 7.1-8.0 | 127-144 | | +4 |
| 8.1-9.0 | 145-162 | | +6 |
| >9.0 | >162 | | +8 |

[a]Based on a single measurement on the day of titration;
[b]Based on the lowest of 3 consecutive days' measurements.
IDeg insulin degludec;
SMBG self-measured blood glucose

TABLE 3

Demographics and baseline characteristics BEGIN™ Once Simple

| Characteristic | IDeg Simple | IDeg Step-wise |
|---|---|---|
| Participants in the full analysis set, n | 111 | 111 |
| Participants in the safety analysis set, n | 110 | 111 |
| Female/Male, n (%) | 43 (38.7)/68 (61.3) | 36 (32.4)/75 (67.6) |
| Ethnic Group: White/Black/Asian, American Indian or Alaska Native/Other, n (%) | 99 (89.2)/8 (7.2)/ 3 (2.7)/1 (0.9) | 97 (87.4)/9 (8.1)/ 2 (1.8)/3 (2.7) |
| Age (years) | 59.4 (±9.5) | 58.5 (±11.1) |
| Body weight (kg) | 95.7 (±18.9) | 91.3 (±18.2) |
| Body mass index (kg/m$^2$) | 33.4 (±5.8) | 31.5 (±5.2) |
| Duration of diabetes (years) | 8.9 (±5.5) | 9.6 (±7.2) |
| HbA$_{1c}$ (%) | 8.1 (±0.9) | 8.2 (±0.9) |
| FPG (mmol/L) | 9.3 (±2.6) | 9.4 (±2.8) |
| (mg/dL) | 167.4 (±46.8) | 169.2 (±50.4) |
| OAD treatment at screening, n (%) | | |
| 1 OAD | 27 (24.3%) | 26 (23.4%) |
| Met | 27 (24.3%) | 26 (23.4%) |
| 2 OADs | 61 (55.0%) | 61 (55.0%) |
| Met + DPP-4I | 16 (14.4%) | 13 (11.7%) |
| Met + Glinide | 1 (0.9%) | 2 (1.8%) |
| Met + SU | 40 (36.0%) | 42 (37.8%) |
| Met + TZD | 4 (3.6%) | 4 (3.6%) |
| 3 OADs | 23 (20.7%) | 24 (21.6%) |
| α-glu inhib + Met + DPP-4I | 1 (0.9%) | — |
| Met + DPP-4I + Glinide | 1 (0.9%) | 3 (2.7%) |
| Met + DPP-4I + SU | 13 (11.7%) | 8 (7.2%) |
| Met + DPP-4I + TZD | — | 2 (1.8%) |
| Met + SU + TZD | 8 (7.2%) | 11 (9.9%) |

Data are presented as number (%) or mean (SD).
OAD oral antidiabetic drug,
Met metformin,
SU sulfonylurea,
TZD thiazolidinedione,
DPP-4I dipeptidyl peptidase 4 inhibitor,
a-glu inhib, alpha-glucosidase inhibitor,
FPG fasting plasma glucose,
IDeg insulin degludec,
SD standard deviation,
HbA$_{1c}$ glycosylated hemoglobin.

TABLE 4

Summary of adverse events BEGIN™ Once Simple

| | IDeg Simple N = 110 | | | | IDeg Step-wise N = 111 | | | |
|---|---|---|---|---|---|---|---|---|
| | N | % | E | R | N | % | E | R |
| AEs | 66 | 60.0 | 181 | 346 | 69 | 62.2 | 197 | 379 |
| AEs occurring with a frequency ≥5% | 17 | 15.5 | 18 | 34 | 14 | 12.6 | 22 | 42 |
| Headache | 8 | 7.3 | 8 | 15 | 8 | 7.2 | 14 | 27 |
| Nasopharyngitis | 10 | 9.1 | 10 | 19 | 7 | 6.3 | 8 | 15 |
| SAEs | 5 | 4.5 | 8 | 15 | 7 | 6.3 | 8 | 15 |

Treatment-emergent events occurring after first exposure and no later than 7 days after last exposure. Safety analysis set. n number of patients with events,
% proportion of patients with events,
E number of events,
R number of events per 100 patient-years.

TABLE 5

Device-specific questionnaire responses BEGIN™ Once Simple

| | Positive response (Category 1 or 2) N (%) | Neutral or Negative response (Category 3, 4 or 5) N (%) |
|---|---|---|
| 1. How easy or difficult do you find it to hold the pen stable when injecting? | | |
| Wk 12 | 195 (94.7) | 11 (5.3) |
| Wk 26 | 202 (98.5) | 3 (1.5) |
| 2. How easy or difficult is it to push down the injection button? | | |
| Wk 12 | 197 (95.2) | 9 (4.8) |
| Wk 26 | 202 (98.0) | 4 (2.0) |
| 3. How easy or difficult is it to turn the dose selector when choosing the right dose? | | |
| Wk 12 | 199 (97.5) | 5 (2.5) |
| Wk 26 | 196 (96.1) | 8 (3.9) |
| 4. How easy or difficult is it to know if the push button has been pushed down completely? | | |
| Wk 12 | 192 (93.2) | 14 (6.8) |
| Wk 26 | 195 (95.2) | 9 (4.8) |
| 5. How easy or difficult is it to see the dose scale when injecting? | | |
| Wk 12 | 176 (85.5) | 30 (14.5) |
| Wk 26 | 174 (85.2) | 30 (14.8) |

TABLE 5-continued

Device-specific questionnaire responses BEGIN™ Once Simple

| | Positive response (Category 1 or 2) N (%) | Neutral or Negative response (Category 3, 4 or 5) N (%) |
|---|---|---|
| 6. How easy or difficult was it to learn how to use this pen? | | |
| Wk 12 | 200 (98.0) | 4 (2.0) |
| Wk 26 | 199 (98.5) | 3 (1.5) |
| 7. How easy or difficult is it to inject your usual insulin dose? | | |
| Wk 12 | 193 (94.6) | 11 (5.4) |
| Wk 26 | 196 (97.0) | 6 (3.0) |
| 8. How easy or difficult is it to reach the dose button when injecting your insulin dose? | | |
| Wk 12 | 193 (94.6) | 11 (5.4) |
| Wk 26 | 195 (96.5) | 7 (3.5) |
| 9. Overall, how confident are you in your management of daily insulin injection using this pen? | | |
| Wk 12 | 191 (93.1) | 14 (6.9) |
| Wk 26 | 196 (96.1) | 8 (3.9) |
| 10. Overall, how confident are you in controlling your blood sugar level using this pen? | | |
| Wk 12 | 167 (81.8) | 37 (18.2) |
| Wk 26 | 178 (88.6) | 23 (11.4) |

Data is based on FAS and summarized independent of treatment arm.
% Percentage based on ITT population who answered the questionnaire.
Categories for questions 1-8: 1 = Very easy, 2 = Somewhat easy, 3 = Neither easy nor difficult, 4 = Somewhat difficult, 5 = Very difficult.
Categories for questions 9-10: 1 = Very, 2 = Quite, 3 = Somewhat, 4 = Not very, 5 = Not at all (confident).
N Number,
Wk Week,
ITT intention to treat.

| | Positive response N (%) | Negative response N (%) |
|---|---|---|
| 1. Did you have any problems using the pen? | | |
| Wk 12 | 205 (100.0) | N/A |
| Wk 26 | 201 (100.0) | N/A |
| 2. Would you recommend the pen? | | |
| Wk 12 | 202 (100.0) | N/A |
| Wk 26 | 200 (100.0) | N/A |

Data is based on FAS and summarized independent of treatment arm.
Categories for questions 1-2: 1 = No, 2 = Yes.
N Number,
Wk Week,
NA not applicable,
ITT intention to treat.

The invention claimed is:

1. An insulin titration method comprising:
   (a) obtaining a fasting blood or plasma sample, or non-invasive glucose measurement from an individual in need of treatment of type 2 diabetes;
   (b) performing a single fasting blood or plasma glucose measurement on the sample obtained in (a);
   (c) using the single fasting blood or plasma glucose measurement obtained in (b) to determine a LysB29 (Nε-hexadecandioyl-γ-Glu) des(B30) human insulin (insulin degludec) dose to be administered; and
   (d) administering said insulin to the individual at the dose determined in step (c);
   wherein subsequent doses of insulin are titrated by repeating step (a) and (b), the measurement being:
   ≤3.9 mmol/L (≤70 mg/dL): the dose administered in step (d) is reduced by 4 U compared to the dose previously administered; or
   4 to 5 mmol/L (71 to 90 mg/dL): the dose administered in step (d) is unaltered compared to the dose previously administered; or
   ≥5.1 mmol/L (≥91 mg/dL): the dose administered in step (d) is increased by 4 U compared to the dose previously administered;
   wherein step (d) is performed for an administration period of at least 3 days between two consecutive titrations; and
   wherein comparable improvements in $HbA_{1c}$ levels are seen relative to titration methods that are based on an average of at least three consecutive fasting blood glucose measurements per week.

2. The method according to claim 1, further comprising the following-step:
   (e) repeating steps (a) to (d).

3. The method according to claim 1, wherein steps (a) to (c) are performed on the same day,
   wherein, in step (d), said insulin is administered for an administration period of at least 3 days, and starting on the same day as steps (a) to (c), and
   wherein said steps (a) to (d) are repeated continuously as long as needed by the said individual in need of treatment.

4. The method according to a claim 1, wherein said insulin is administered, either concurrently or consecutively, with one or more additional drugs used in the treatment of diabetes.

5. The method according to claim 4 wherein said insulin is administered concurrently or consecutively with liraglutide.

* * * * *